United States Patent [19]

Testa et al.

[11] Patent Number: 5,676,942
[45] Date of Patent: Oct. 14, 1997

[54] COMPOSITION CONTAINING HUMAN ALPHA INTERFERON SPECIES PROTEINS AND METHOD FOR USE THEREOF

[75] Inventors: Douglas Testa, Neshanic Station; Mei-June Liao, Monmouth Junction; Katalin Ferencz-Biro, North Brunswick; Abbas Rashidbaigi, Morris Plains, all of N.J.; Mario DiPaola, Bayside, N.Y.

[73] Assignee: Interferon Sciences, Inc., New Brunswick, N.J.

[21] Appl. No.: 454,444

[22] Filed: May 25, 1995

Related U.S. Application Data

[63] Continuation of Ser. No. 144,601, Oct. 27, 1993, abandoned, which is a continuation-in-part of Ser. No. 129,089, Oct. 5, 1993, Pat. No. 5,503,828, which is a continuation-in-part of Ser. No. 835,030, Feb. 10, 1992, abandoned.

[51] Int. Cl.$^6$ .................................................. A61K 38/21
[52] U.S. Cl. .................. 424/857; 424/85.4; 514/2; 514/21; 530/351; 435/70.5
[58] Field of Search .................. 424/85.7, 85.4; 514/2, 21; 435/70.5; 530/351

[56] References Cited

U.S. PATENT DOCUMENTS

| | | | |
|---|---|---|---|
| 4,289,690 | 9/1981 | Pestka et al. | 424/85.4 |
| 4,414,150 | 11/1983 | Goeddel | 435/68 |
| 4,503,035 | 3/1985 | Pestka et al. | 424/85.4 |
| 4,530,901 | 7/1985 | Weissmann | 435/70 |
| 4,636,383 | 1/1987 | Nagabhushan | 424/85.4 |
| 4,656,131 | 4/1987 | Kitano et al. | 435/68 |
| 4,696,899 | 9/1987 | Toth et al. | 435/68 |
| 4,780,530 | 10/1988 | Teraoka et al. | 530/351 |
| 4,791,101 | 12/1988 | Adolf | 514/2 |
| 4,820,514 | 4/1989 | Cummins | 424/85.4 |
| 4,885,166 | 12/1989 | Meyer et al. | 424/85.7 |
| 4,911,908 | 3/1990 | Estis et al. | 424/85.4 |
| 4,975,276 | 12/1990 | Innis | 424/85.7 |
| 5,019,382 | 5/1991 | Cummins | 424/85.4 |
| 5,098,703 | 3/1992 | Innis | 424/85.7 |
| 5,165,921 | 11/1992 | Ganesh et al. | 424/85.7 |
| 5,372,808 | 12/1994 | Blatt et al. | 424/85.4 |
| 5,503,828 | 4/1996 | Zesta et al. | 424/85.7 |

FOREIGN PATENT DOCUMENTS

| | | |
|---|---|---|
| 018218 | 10/1980 | European Pat. Off. |
| 091543 | 10/1983 | European Pat. Off. |
| WO83/00693 | 3/1983 | WIPO |
| WO86/06744 | 11/1986 | WIPO |
| WO93/16107 | 8/1993 | WIPO |

OTHER PUBLICATIONS

D. Goeddel et al, "The Structure of Eight Distinct Cloned Human Leukocyte Interferon cDNAs", *Nature*, 290:20–26 (Mar. 5, 1981) [Goeddel I].

D. Bowden et al, "Cloning of Eukaryotic Genes in Single-Strand Phage Vectors: the Human Interferon Genes", *Gene*, 27:87–99 (1984).

O. Ohara et al, "Anomalous Behavior of Human Leukocyte Interferon Subtypes on Polyacrylamide Gel Electrophoresis in the Presence of Dodecyl Sulfate", *FEBS Letters*, 211(1):78–82 (Jan., 1987).

A. Friedman-Kien et al, "Natural Interferon Alpha for Treatment of Condylomata Acuminata", *JAMA*, 259(4):533–538 (Jan. 22/29, 1988).

"Intron A" Physicians Desk Reference, 47th edit., eds. Medical Economics Data, Montvale, NJ, pp. 2194 and 2006 (Dec., 1992).

M. Khan et al, "Inhibition of Growth, Transformation, and Expression of Human Papillomavirus Type 16 E7 in Human Keratinocytes by Alpha Interferons", *J. Virol.*, 67(6):3396–3403 (Jun., 1993).

S. Sperber et al, "Anti-HIV-1 Activity of Recombinant and Hybrid Species of Interferon-alpha", *J. Interferon Res.*, 12(5):363–368 (Oct. 14, 1992).

H. Hochkeppel et al, "Murine AIDS: Effect of a rHu Interferon Alpha-B/D Hybrid (IFN) Against Herpes Simplex Virus Superinfection", *J. Cellular Biochem.*, Suppl. 14D, UCLA Symposia on Molecular and Cellular Biology, Abstracts, 19th Annual Meetings, Abstract L319, p. 136 (Mar. 11–Apr. 6, 1990).

J. Gangemi et al, "9–(2–Phosphonylmethoxyethyl) Adenine in the Treatment of Murine Acquired Immune Deficiency Disease and Opportunistic Herpes Simplex Virus Infections", *Antimicrobial Agents and Chemotherapy*, 33(11):1864–1868 (Nov., 1989) [Gangemi I].

H. Lane et al, "Interferon-alpha in Patients with Asymptomatic Human Immunodeficiency Virus (HIV) Infection", *Annals of Internal Medicine*, 112(11):805–811 (Jun. 1, 1990).

S. Pestka, "Interferons–Part A", *Meth. Enzymol.*, 78:22–23 (1981) [Pestka I].

K. Zoon, "Purification and Characterization of Human Interferon from Lymphoblastoid (Namalva) Cultures", *Meth. Enzymol.*, 78:457–465 (1981) [Zoon I].

M.-J. Liao et al, "Absence of Neutralizing Antibodies to Interferon in Condyloma Acuminata and Cancer Patients Treated with Natural Human Leukocyte Interferon", *J. Infect. Dis.*, 165:757–760 (Apr., 1992).

T. Khavkin et al, "Interactions of Human Monoblastoid Cells (U937) with Sendai Virus and Induction of alpha-Interferon", *J. Leukocyte Biology, 1992 Annual Meeting Abstracts*, Suppl. 3, Abstr. 137:36 (Oct. 22, 1992).

M. Padhye et al, "Optimization of Interferon Production from Human Peripheral Blood Leukocytes", *Keynote Symposia in Growth Factors and Inhibitors*, (Jan. 26–Feb. 2, 1992).

(List continued on next page.)

Primary Examiner—Chhaya D. Sayala
Attorney, Agent, or Firm—Howson and Howson

[57] ABSTRACT

This invention provides alpha interferon compositions comprising one or a mixture of selected highly antiviral interferon proteins, which compositions are characterized by increased anti-viral activity. These compositions may be used therapeutically in the treatment of viral infection, particularly retroviral or hepatitis infection or as additives to conventional antiviral agents to increase the antiviral potency thereof.

22 Claims, 2 Drawing Sheets

OTHER PUBLICATIONS

G. Linette et al, "Inactivation of HIV-1 in Preparations of Human Interferon by Low pH Treatment", *Cancer Therapy and Control*, 1:109–120 (1990).

H. Axelrod et al, "Trace Amounts of Murine Immunoglobulin in Affinity Purified Leukocyte Interferon Alpha are not Immunogenic", *Biotechnology Ther.*, 3(1&2):35–49 (Apr. 2, 1992) [Axelrod I].

R. Wells et al, "Interferon–anl in Children with Recurrent Acute Lymphocytic Leukemia: A Phase I Study of Pharmacokinetics and Tolerance", *J. Interferon Res.*, 8:309–318 (1988).

A. Billiau, "Interferon Therapy: Pharmacokinetic and Pharmacological Aspects", *Arch. Virol.*, 67:121–133 (1981).

G. Dusheiko et al, "Recombinant Leukocyte Interferon Treatment of Cronic Hepatitis B", *Hepatology*, 5(4):556–560 (1985).

P. Burman et al, "Thyroid Autoimmunity in Patients on Long Term Therapy with Leukocyte–Derived Interferon", *J. Clin. Endocrinology and Metabolism*, 63(5):1086–1090 (1986).

M. Talpaz et al, "Hematologic Remission and Cytogenic Improvement Induced by Recombinant Human Interferon AlphaA in Chronic Myelogenous Leukemia", *New England J. Med.*, 314(17):1065–1069 (Apr. 24, 1986).

G. Scott et al, "Skin Reactions to Interferon Inoculations are Reduced but not Abolished by Purification", *J. Interferon Res.*, 1(1):79–85 (1980).

F. Barouki et al, "Time Course of Interferon Levels, Antiviral State, 2',5'–Oligoadenylate Synthetase and Side Effects in Healthy Men", *J. Interferon Res.*, 7:29–39 (1987).

R. Wills et al, "Interferon Kinetics and Adverse Reactions after Intravenous, Intramuscular, and Subcutaneous Injection", *Clin. Pharmacol. Ther.*, 35(5):722–727 (May, 1984).

G. Jones et al, "Safety and Tolerance of Recombinant Interferon Alfa–2a (Roferon–A) in Cancer Patients", *Cancer*, 57:1709–1715 (Apr. 15, 1986).

H.–G. Klingemann et al, "Treatment with Recombinant Interferon (alpha–2beta) Early After Bone Marrow Transplantation in Patients at High Risk for Relapse", *Blood*, 78(12):3306–3311 (Dec. 15, 1991).

R. Reichel et al, "Clinical Study with Recombinant Interferon Gamma Versus Interferon–Alpha–2c in Patients with *Condylomata acuminata*", *J. STD & AIDS*, 3:350–354 (Sep./Oct., 1992).

T. Taguchi, "Clinical Studies of Recombinant Interferon Alfa–2a (Roferon–A) in Cancer Patients", *Cancer*, 57:1705–1708 (1986).

R. Speigel, "Clinical Overview of Alpha Interferon", *Cancer*, 59:626–631 (1987).

J. Gangemi et al, "Antiviral Activity of a Novel Recombinant Human Interferon–aB/D Hybrid", *J. Interferon Res.*, 9:227–237 (1989) [Gangemi II].

S. Pestka et al, "Interferons and Their Actions", *Ann. Rev. Biochem.*, 56:727–777 (1987) [Pestka II].

S. Nagata et al, "Synthesis in *E. coli* of a Polypeptide with Human Leukocyte Interferon Activity", *Nature*, 284:316–310 (Mar. 27, 1980).

A. Mizrahi, "Production of Human Lymphoblastoid (Namalva) Interferon", *Meth. Enzymol.*, 78:54–68 (1981).

A. Phillips et al, "Large–Scale Production of Human Interferon from Lymphoblastoid Cells", *Meth. Enzymol.*, 119:35–38 (1986).

K. Mogensen et al, "Production and Preparation of Human Leukocyte Interferon", *Pharmacol. Ther. C*, 1:369–381 (1977).

K. Cantell et al, "Production of Interferon in Human Leukocytes from Normal Donors with the Use of Sendai Virus", *Methods Enzymol.*, 78:29–38 (1981) [Cantell I].

B. Horowitz, "Large–Scale Production and Recovery of Human Leukocyte Interferon from Peripheral Blood Leukocytes", *Methods Enzymol.*, 119:39–47 (1986).

P. Weck et al, "Interferons in the Treatment of Genital Human Papillomavirus Infections", *Am. J. Med.*, 85(Suppl 2A):159–164 (Aug. 29, 1988) [Weck I].

J. Korenman et al, "Long–Term Remission of Chronic Hepatitis B After Alpha–Interferon Therapy", *Annal. Intern. Med.*, 114(8):629–634 (Apr. 15, 1991).

S. Baron et al, "Special Communications–The Interferons–Mechanisms of Action and Clinical Applications", *JAMA*, 266(10):1375–1383 (Sep. 11, 1991).

M. Hirsch, "Antiviral Drug Development for the Treatment of Human Immunodeficiency Virus Infections (An Overview)", *Am. J. Med.*, 85(Suppl 2A):182–185 (Aug. 29, 1988).

P. Weck et al, "Antiviral Activity of Bacteria–Derived Human Alpha Interferons Against Encephalomyocarditis Virus Infection of Mice", *Infect. Immun.*, 35(2):660–665 (Feb., 1982) [Weck II].

E.–D. Kreuser et al, "Modulation of Integrin Expression by Cytokines on Colon Cancer Cell Lines", *Onkologies*, 14(Suppl. 2), Abstract No. 270, p. 92 (1991).

H. Harada et al, "Distinction of Two Subtypes of Human Leukocyte Interferon (IFN–a) on B Cell Activation, B Cell Proliferation of Two Subtypes of IFN–a", *J. Immunol.*, 131(1):238–243 (Jul., 1983).

D. Goeddel et al, "Human Leukocyte Interferon Produced by *E. coli* is Biologically Active", *Nature*, 287:411–416 (Oct. 2, 1980) [Goeddel II].

M. Streuli et al, "At Least Three Human Type a Interferons: Structure of a2", *Science*, 209:1343–1347 (Sep. 19, 1980).

A. Lok et al, "Interferon Antibodies May Negate the Antiviral Effects of Recombinant a–Interferon Treatment in Patients with Chronic Hepatitis B Virus Infection", *Hepatology*, 12(6):1266–1270 (1990).

S. Jacobs et al, "Minimal Antigenicity of Intron A in Human Recipients Demonstrated by Three Analytical Methods", *J. Biol. Resp. Mod.*, 7:447–456 (1988).

P. Weck et al, "Detection and Incidence of Neutralizing Antibodies to Interferon–a–n1", *J. Interferon Res.*, 9(Suppl 1):S37–S43 (1989) [Weck III].

P. Von Wussow et al, "Clinical Significance of Anti–IFN–a Antibody Titres During Interferon Therapy", *Lancet*, 2:635–636 (Sep. 12, 1987).

K. Cantell et al, "Partial Purification of Human Leukocyte Interferon on a Large Scale", *Meth. Enzymol.*, 78:499–512 (1981) [Cantell II].

K. Berg et al, "Antibody Affinity Chromatography of Human Leukocyte Interferon", *Meth. Enzymol.*, 78:487–499 (1981).

H. R. Axelrod et al, "Assessment of Anti–Interferon Antibodies in Patients Receiving Immunoaffinity Purified Human Interferon Alpha (ALFERON)", *Future Development of Interferon*, Proceedings 1988 Annual Meeting of the International Society for Interferon Research, Post Sumiferon Symposium, Sumitomo Pharmaceuticals Co., Ltd., publ. (Nov. 19, 1988) [Axelrod II].

Product Information, ALFERON N INJECTION, Interferon alfa-n3 (Human Leukocyte Derived) (1989).

K. Berg et al, "Purification of Human Interferon by Antibody Affinity Chromatography, using Highly Absorbed Anti-interferon", *Scand. J. Immunol.*, 8:429–436 (May, 1978) [Berg II].

L. Lin et al, "Purification of Human Leukocyte Interferon by Two–Dimensional Polyacrylamide Gel Electrophoresis", *Meth. Enzymol.*, 78:481–487 (Dec. 18, 1981) [Lin I].

L. Lin et al, "Purification of Human Leukocyte Interferon to Apparent Homogeniety: Criteria for Purity", *Abstr. Ann. Meeting American Soc. for Microbiol.*, S203 (May 14–19, 1978) [Lin Ii].

S. Pestka, "The Human Interferons–From Protein Purification and Sequence to Cloning and Expression in Bacteria: Before, Between, and Beyond", *Arch. Biochem. Biophys.*, 221(1):1–37 (Feb. 15, 1983) [Pestka III].

L. Lin et al, "Characterization of the Heterogeneous Molecules of Human Interferons: Differences in the Cross–Species Antiviral Activities of Various Molecular Populations in Human Leukocyte Interferons", *J. Gen. Virol.*, 39:125–130 (Apr., 1978) [Lin III].

E. Fish et al, "Human Leukocyte Interferon Subtypes have Different Antiproliferative and Antiviral Activities on Human Cells", *Biochem. Biophys. Res. Comm.*, 112(2):537–546 (Apr. 29, 1983).

V. Savel 'ev et al, *Antibiot. Med. Biotekhnol.*, 31:592–596 (1986).

K. Henco et al, "Structural Relationship of Human Interferon Alpha Genes and Pseudogenes", *J. Mol. Biol.*, 185:227–260 (1985).

S. Cohen et al, "Cloning, Expression and Biological Activity of a New Variant of Human Interferon a Identified in Virus Induced Lymphoblastoid Cells", *Develop. Biol. Standard*, 60:111–122 (1985).

J. Mizoguchi et al, "Efficient Expression in *Escherichia coli* of Two Species of Human Interferon–a and Their Hybrid Molecules", *DNA*, 4(3):221–232 (1985).

A. Ovchinikov et al, *Doklady Akad, Nauk, S.S.S.R.*, 262:725–728 (1982).

E. Rehberg et al, "Specific Molecular Activities of Recombinant and Hybrid Leukocyte Interferons", *J. Biol. Chem.*, 257(19):11497–11502 (Oct. 10, 1982).

G. Sen et al, "Antiviral and Protein–Inducing Activities of Recombinant Human Leukocyte Interferons and Their Hybrids", *J. Virol.*, 50(2):445–450 (May, 1984).

J. Greiner et al, "Differential Effects of Recombinant Human Leukocyte Interferons on Cell Surface Antigen Expression", *Cancer Research*, 46:4984–4990 (Oct., 1986).

B–L. Li et al, "a–Interferon Structure and Natural Killer Cell Stimulatory Activity", *Cancer Research*, 50:5328–5332 (Sep. 1, 1990).

N. Finter, "Why are There so many Subtypes of Alpha–Interferons?", *J. Interferon Res., Special Issue:*185–194 (Jan., 1991).

A. Greenway et al, "Selective Production of Interferon–alpha Subtypes by Cultured Peripheral Blood Mononuclear Cells and Lymphoblastoid Cell Lines", *Immunol.*, 75:182–188 (1992).

T. Goren et al, "High and Low Potency Interferon–a Subtypes Induce (2'–5') Oligoadenylate Synthetase with Similar Efficiency", *Virol.*, 130:273–280 (1983) [Goren I].

P. Weck et al, "Comparison of the Antiviral Activities of Various Cloned Human Interferon–a Subtypes in Mammalian Cell Cultures", *J. Gen. Virol.*, 57:233–237 (1981) [Weck IV].

M. Rubinstein, "Multiple Interferon Subtypes: The Phenomenon and its Relevance", *J. Interferon Res.*, 7:545–551 (1987).

T. Goren et al, "Human Monocytes and Lymphocytes Produce Different Mixtures of a–Interferon Subtypes", *J. Interferon Res.*, 6:323–329 (1986) [Goren II].

I. Heron et al, "13 Native Human Interferon–Alpha Species Assessed for Immunoregulatory Properties", *J. Interferon Res.*, 3(2):231–239 (1983).

S. Kojima et al, "Purification and Characterization of Human Interferon–a Subtypes from Namalwa Lymphoblastoid Cells", *J. Interferon Res.*, 9(Suppl. 2):S178, Abstract No. A4–8 (1989).

S. Fukuda et al, "Simultaneous Production of Natural Human Tumor Necrosis Factor–a, –b and Interferon–a from BALL–1 Cells Stimulated by HVJ", *Lymphokine Research*, 7(2):175–185 (1988).

K. Zoon et al, "Chemical and Biological Characterization of Natural Human Lymphoblastoid Interferon Alphas", pp. 567–569 (undated) [Zoon II].

Physician's Desk Reference, "WELLFERON, Interferon Alpha–n1 (Ins) Injection".

B. Cheetham et al, "Structure–function Studies of Human Interferons–a: Enhanced Activity on Human and Murine Cells", *Antiviral Research*, 15:27–40 (1991).

J. Langer et al, "Binding of Human Alpha–Interferons to Natural Killer Cells", *J. Interferon Res.*, 6:97–105 (1986) [Langer II].

O. Merimsky et al, "Pharmacokinetics of Recombinant Interferon Alpha–C", *Cancer Chemother. Pharmacol.*, 27:406–408 (1991). [Merimsky I]

O. Merimsky et al, "The Use of Interferon Alpha–C in Patients with Metastatic Renal Cell Carcinoma Arising in a Congenital Solitary Kidney", *J. Surg. Oncol.*, 45(4):279–281 (Dec., 1990) [Merimsky II].

D. Aderka et al, "Recombinant Interferon Alpha–C for Advanced Hairy Cell Leukemia", *Cancer*, 61:2207–2213 (1988).

E. Gren et al, "Novel Human Leukocyte Interferon Subtype and Structural Comparison of Alpha Interferon Genes", *J. Interferon Res.*, 4:609–617 (1984).

R. Wills et al, "Pharmacokinetics of Human Recombinant Interferon–aI after iv Infusion and im Injection in African Green Monkeys", *J, Interferon Res.*, 8:427–432 (1988).

E. Lundgren et al, "Interferon–a: a Gene Family in Therapeutic Use", *J. Pharm. Biomed. Anal.*, 7(2):233–238 (1989).

K. Zoon et al, "Purification and Partial Characterization of Human Lymphoblastoid Interferon", *Proc. Nat., Acad. Sci. USA*, 76(11):5601–5605 (Nov., 1979) [Zoon III].

K. Zoon et al, "Purification and Characterization of Multiple Components of Human Lymphoblastoid Interferon–a", *J. Biol. Chem.*, 267(21):15210–15216 (Jul. 25, 1992) [Zoon IV].

M. DiPaola et al, "Natural Human Leukocyte Interferon (Interferon alfa–n3) Contains Interferon a2b, not a2a or a2c," Abstract only, Poster Presentation, *FASEB* (Feb. 9–13, 1992) [DiPaola I].

M. DiPaola et al, "Interferon a2 Subtypes in Natural Human Leukocyte Interferon (Interferon alfa–n3)", Abstract only, presented at ISIR Meeting, Toronto (1992) [DiPaola II].

T. Smith et al, "Tryptic Peptide Mapping Demonstrates Conformational Differences Among Human IFN–a Subtypes", Abstract only, presented at FASEB Meeting, Houston, Texas (1992) [Smith I].

F. Adams et al, "Neuropsychiatric Manifestations of Human Leukocyte Interferon Therapy in Patients with Cancer", JAMA, 252(7):938–941 (Aug. 17, 1984).

N. Lee et al, "Expression of Two Different Human Interferon Genes in One Vector", Abstract only, DNA (Feb., 1987) [Lee II].

T. Smith et al, "Fingerprinting Natural Human Alpha Interferon Subtypes by Tryptic HPLC Mapping", Abstract only, Poster Presentation, FASEB (Feb.9–13, 1992) [Smith II].

Product Literature, "The First Natural–Source, Multi–subspecies Alpha Interferon Counterattack Against HPV6, 11", ALFERON N Injection Interferon alfa–n3 (Human Leukocyte Derived) (1990).

Product Literature, "The First Natural–Source, Multi–subspecies Alpha Interferon, A Significant Advance in the Treatment of Refractory or Recurrent Condylomata Acuminata (genital warts)", ALFERON N Injection Interferon alfa–n3 (Human Leukocyte Derived) (Oct., 1990).

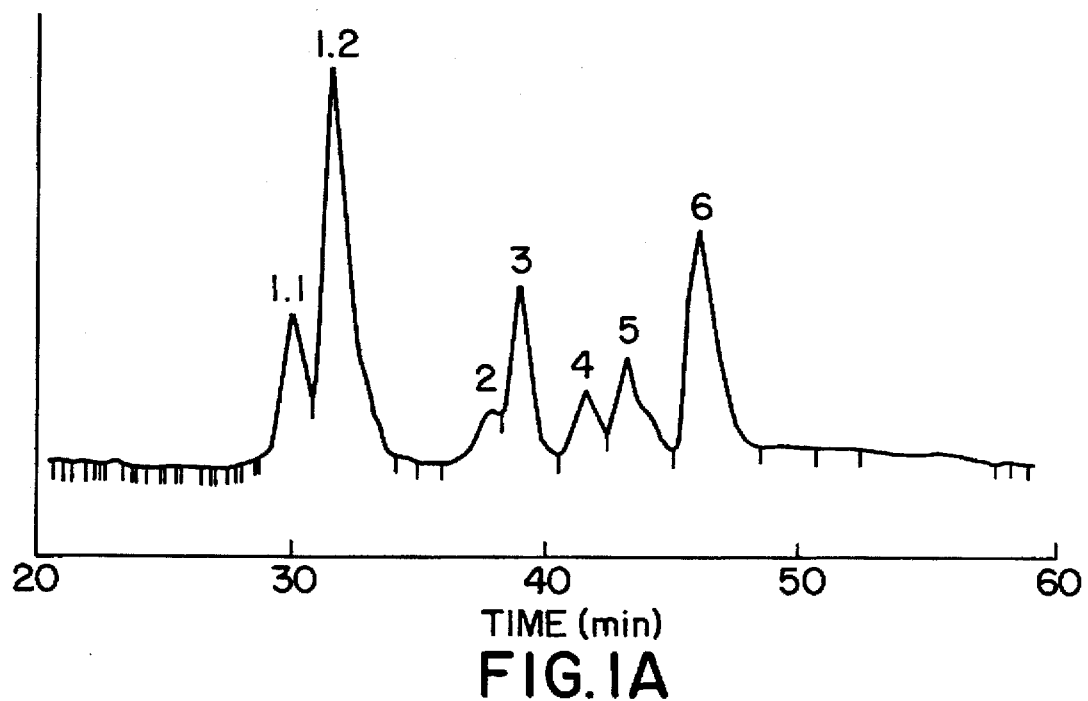
FIG. IA
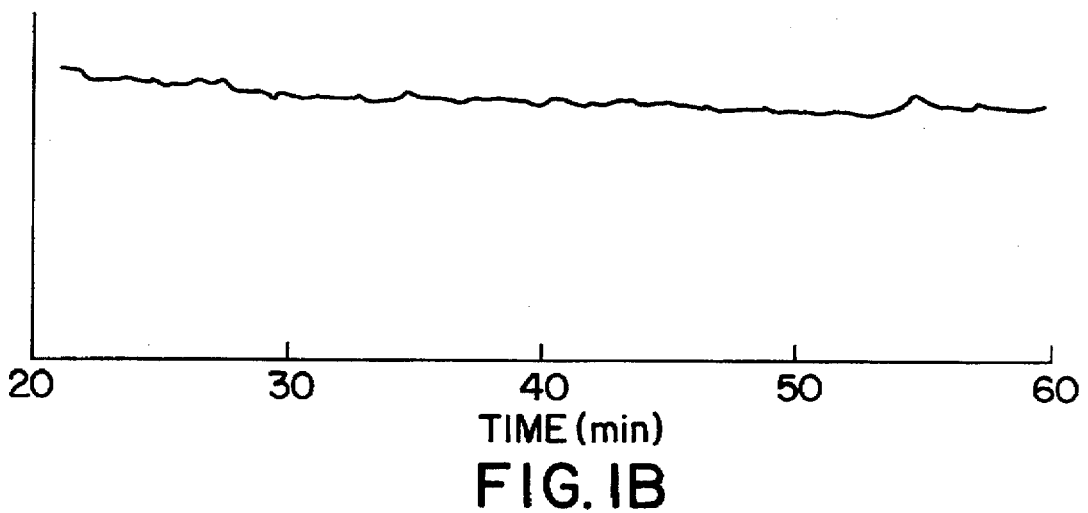
FIG. IB

COMPOSITION CONTAINING HUMAN ALPHA INTERFERON SPECIES PROTEINS AND METHOD FOR USE THEREOF

CROSS-REFERENCE TO OTHER APPLICATIONS

This is a continuation of U.S. patent application Ser. No. 08/144,601, filed Oct. 27, 1993, now abandoned, which is a continuation-in-part of U.S. patent application Ser. No. 129,089, filed Oct. 5, 1993, now U.S. Pat. No. 5,503,828 which is a continuation-in-part of U.S. patent application Ser. No. 835,030, filed Feb. 10, 1992 abandoned.

FIELD OF THE INVENTION

This invention relates generally to a human alpha interferon composition characterized by an enhanced antiviral potency, particularly against retroviral infections, which composition may be employed alone as a pharmaceutical composition or as an additive to known antiviral agents to increase the anti-viral potency of the resulting pharmaceutical composition.

BACKGROUND OF THE INVENTION

Human alpha interferons (also known as Leukocyte interferons) comprise a family of about 30 protein species, encoded by at least 14 different genes and about 16 alleles. Some of these alpha interferon protein species have been shown to have antiviral, antigrowth and immunoregulatory activities [See, e.g., Pestka et al., *Ann. Rev. Biochem.*, 56:727 (1987)].

Although the nomenclature has changed, interferon species are referred to by letters and numbers in the various publications. The currently accepted correspondence of these designations is as follows in the Table 1 below:

TABLE 1

| Correspondence of IFN Nomenclature | | | |
|---|---|---|---|
| Letter | Numerical | Letter | Numerical |
| αA | α2a | αM | α4a |
|  | α2b |  |  |
|  | α2c |  | α4b |
| αB | α8a | αMI | α4a |
| αB' | α8c |  |  |
| αB2 | α8b | αN | α14c |
| αC | α10a | αO | α16 |
| αD | α1a | αI | α17a |
|  | α1b | αI' | α17b |
| G | α5 |  | 88 or α17c |
| αH | α14a | II | α17d |
| αJ | α7a | αf | α21a |
| αJ1 | α7c |  |  |
| αJ2 | α7b | α(Ovch) | α21b |
| αK | α6 |  |  |

The sequences of all of these interferon species are available on a variety of commercial databases, including the Genbank® database [Intell Genetics, Inc., Mountain View, Calif.], as well as by reference to the art [see, e.g., D. V. Goeddel et al, *Nature*, 290:20–26 (Mar. 5, 1981); Nagata et al, *Nature*, 284:3126–320 (1980); D. W. Bowden et al, *Gene*, 27:87–99 (1984); and O. Ohara and H. Teraoka, *FEBS Letters*, 211(1):78–82 (January 1987)].

Products containing recombinant interferons have been produced which consist of a single species of interferon protein. For example, IFN-α2 is the recombinant human alpha interferon protein species in the commercially available products, Intron® A (IFN alfa-2b) [Schering Plough] and Roferon® A (IFN alfa-2a) [Hoffman-La Roche].

However, interferons derived from natural sources are also provided, which include substantial amounts of IFN-α2, generally in excess of 50% by weight of available protein, in the presence of multiple other naturally occurring IFN-α species. Such interferon compositions include those purified from human lymphoblastoid, Namalwa, cell line [Mizrahi, *Meth. Enzymol.*, 78:54 (1981); and Phillips et al., *Meth. Enzymol.*, 119:35 (1986)]. Other natural IFN-α mixtures are those products isolated and purified from human peripheral blood leukocytes [Mogensen et al., *Pharmacol Ther. Part C,* 1:369 (1977); Cantell et al., *Methods Enzymol.*, 78:29 (1981); Horowitz, *Methods Enzymol.*, 119:39 (1986); and the commercial product, Alferon® N, which contains about 48% IFN-α2 (interferon Sciences, Inc.)]. See also IFN-αn3a, which is an improved natural mixture of alpha interferon species related to Aileron® N and derived from human peripheral blood leukocytes, described in International PCT Publication No. WO93/16107, published Aug. 19, 1993, and further discussed herein.

Due to the natural abundance of IFN-α2, alpha interferon pharmaceutical preparations presently in use for the treatment of a variety of conditions contain predominantly the IFN-α2 species proteins, either prepared as substantially pure recombinant proteins or in the mixtures isolated and purified from natural sources. These compositions have been found to have therapeutic efficacy for human cancers and certain viral diseases. For example, the recombinant interferons (INF alfa-2a, IFN alfa-2b, IFN alfa-2c), as well as mixtures of interferons such as cell-line derived interferon (IFN alfa-n1) and interferon derived from leukocytes (IFN alfa-n3) are currently used for the treatment of *Condyloma acuminata*, hepatitis [Weck et al., *Am. J. Med.*, 85(Suppl 2A):159 (1988); Korenman et al., *Annal. Intern. Med.*, 114:629 (1991); Friedman-Kien et al., *JAMA,* 259:533 (1988)], for the regression of some malignancies [Baron et al., *JAMA,* 266:1375 (1991)], for the treatment of AIDS related Kaposi's sarcoma [Physicians Desk Reference, 47th edit., eds. Medical Economics Data, Montvale, N.J., p. 2194 and 2006 (1993)] and are currently in clinical studies for the treatment of human acquired immunodeficiency syndrome (AIDS) either alone or in combination with other antiviral agents [Hirsch, *Am. J. Med.*, 85(Suppl 2A):182 (1988)].

The limited numbers of studies on IFN-α protein species other than IFN-α2 or on recombinant hybrid proteins formed by fusing portions of natural protein species together have not provided evidence of any substantial therapeutic utility. For example, IFN-α8 has been observed to inhibit the transformation of human keratinocytes by human papillomavirus HPV type 16 (HPV16), and to inhibit HPV16 E7 protein expression [M. Khan et al, *J. Virol.*, 67(6) :3396–3403 (1993)]. IFN-α8 has also been studied for its activity against encephalomyocarditis virus in mice [P. Weck et al, *Infect. Immun.*, 35(2):660–665 (1982)]. IFN-α8 in combination with folinic acid and 5-fluorcuracil was also studied in connection with the treatment of metestatic colorectal cancer [E-D Kreuser et al, *Onkologies,* 14(Suppl. 2), (1991)]. H. Harada et al, *J. Immunol.*, 131(1):238–243 (1983) describes the ability of IFN-α8 to act as an inhibitor of cell proliferation, in contrast to IFN-α2 which was observed to enhance cell proliferation.

Also, for example, anti-HIV activities have been studied in vitro for recombinant interferon-α species, including αA, αD, αJ, αC, αB, αK, and the recombinant hybrid proteins αJ/C and αA/D [S. Sperber et al, *J. Interferon Res.*, 12:363–368 (1992)]. According to this latter study when equal amounts of IFN-α species units were used, IFN-α2a (αA) had significantly higher anti-viral activity than other species. A recombinant hybrid protein, αB/D, (formed of a portion of α8a fused to a portion of α1b) has been noted to have potential advantage for the treatment of HSV and AIDS, [Hochkeppel and Conzens, *J. Cellular Biochem.*, Suppl. 14D, UCLA Symposia on Molecular & Cellular Biology, Abstracts, 19th Annual Meetings, Mar. 11–Apr. 6, 1990, Abstract L319, p.136]. J. D. Gangemi et al, *Antimicrobial Agents and Chemotherapy*, 33(11):1864–1868 (November 1989) describes the therapeutic activity of rHuIFN-αB/D, PMEA and AZT in the treatment of murine AIDS.

Most of these IFN-α compositions have been characterized by a number of side effects in patients, including without limitation, fever, low blood cell counts, gastrointestinal disorders, such as vomiting and diarrhea, renal disorders, pulmonary disorders, allergic reactions, such as bronchospasm or anaphylaxis or skin rashes, hair loss, and infection, which are identified in the product literature for alpha interferens now on the market. While some of the side effects are minor, they can have serious negative impacts on patients who must take significant doses of the compositions for long periods of time. For example, for certain therapies, e.g., Eke treatment of AIDS-related Kaposi's sarcoma and asymptomatic AIDS, the dosage at which the interferons are effective produces side effects which are worse than the effects of the disease at certain stages. In clinical trials for these indications, the occurrence of the side effects has resulted in patients abandoning the procedure despite its probable long term benefit [H C. Lane et al, *Annals of internal Medicine*, 112:805 (1990)].

Thus, there remains a need for improved alpha interferon compositions which can be characterized by low toxicity, high activity and high purity and which can produce minimal side effects in patients undergoing interferon therapy.

SUMMARY OF THE INVENTION

In one aspect, the invention provides an antiviral composition characterized by an enhanced antiviral potency against retroviral or hepatitis infections. The composition contains at least one, or a mixture of, certain human alpha interferon protein species selected from a group characterized by high anti-viral activity. These selected interferon species include α4a, α4b, α7a, α7b, α7c, α8a, α8b, α8c, α10a, α16, α17a, α17b, α17c, α17d, α21a, α21b and combinations thereof. These compositions may optionally contain small amounts of an IFN-α2 protein species. The pharmaceutical composition may further be in admixture with any other conventional pharmaceutical agents or carriers useful in the antiviral compositions.

In yet another aspect, the invention provides a composition including a known antiviral agent and an amount of the antiviral composition as described above sufficient to increase the potency of the known antiviral agent.

In yet another aspect, this invention is directed to a method for treating a mammalian host having a retroviral or hepatitis infection which includes administering the above-described antiviral alpha interferon pharmaceutical compositions, either alone or in conjunction with other drugs. The method is characterized by enhanced antiviral activity against the causative agent of such diseases.

Still a further aspect of this invention is a method for enhancing the potency of a pharmaceutical antiviral composition by adding to that composition an effective amount of the antiviral composition described above.

Other aspects and advantages of the present invention are described further in the following detailed description of preferred embodiments of the present invention.

BRIEF DESCRIPTION OF THE DRAWINGS

In FIG. 1A depicts a typical RP-HPLC profile of IFN-αn3a from a semi-preparative $C_4$ column (10×250 mm), illustrating peaks 1.1, 1.2, and 2 through 6.

In FIG. 1B depicts a comparative blank gradient RP-HPLC profile.

DETAILED DESCRIPTION OF THE INVENTION

Figure 2:
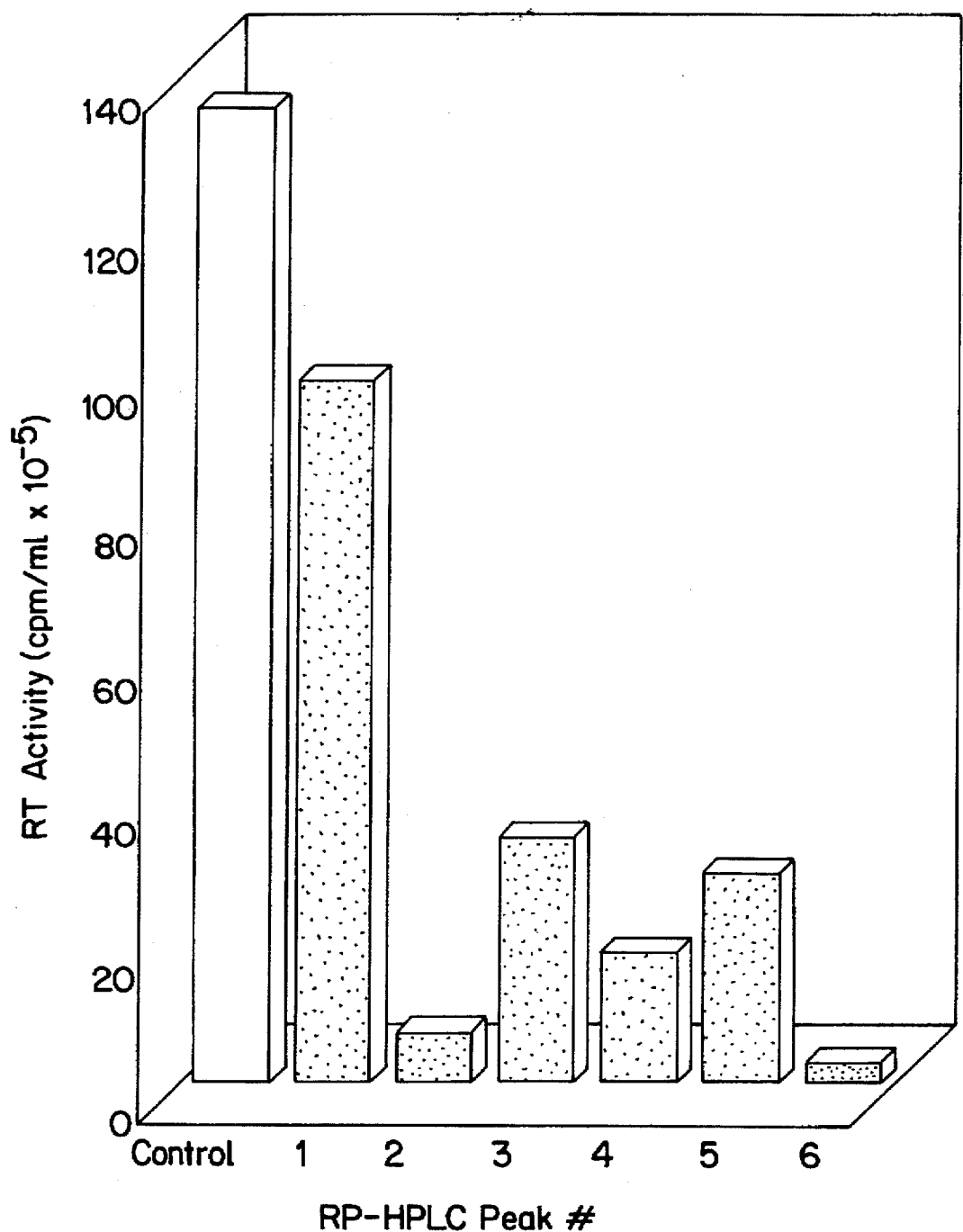
FIG. 2 depicts the relative anti-HIV-1 activities of the RP-HPLC peaks 1 through 6 of IFN-αn3a as discussed in Example 7.

The present invention provides improved alpha interferon compositions which are characterized by enhanced antiviral potency in comparison to single species IFN-α2 protein compositions and known mixtures of IFN-α species. The compositions of this invention may be used alone as antiviral pharmaceutical compositions, particularly for use against viral infections caused by retrovirus or hepatitis strains. Alternatively, the compositions of this invention may be used as additives to known antiviral pharmaceutical compositions to enhance the antiviral potency and reduce the required dosages thereof.

The compositions of this invention differ from naturally occurring and purified interferon mixtures, in that they contain interferon species having a high anti-viral potency selected from the group consisting of α4a, α4b, α7a, α7b, α7c, α8a, α8b, α8c, α10a, α16, α17a, α17b, α17c, α17d, α21a, α21b and combinations thereof. These interferon species are referred to herein as "highly antiviral" interferon species. Preferably these compositions do not contain naturally occurring interferon species with low activity. These compositions are desirable for use in methods for therapeutically treating diseases susceptible to alpha interferon treatment, particularly, retroviral diseases and Hepatitis infections in humans because of their high antiviral potencies. The compositions of this invention enable the use of lower dosages of conventionally employed antiviral agents when in combination therewith.

The compositions of the present invention whether used alone or as additives to other antiviral compositions may be characterized by lower toxicity than prior art interferon pharmaceuticals. For example, the inventors have surprisingly noted that the compositions of the present invention containing an effective amount of at least one or more of the above-listed selected IFN-α species, display a greater efficacy than do the known antiviral compositions containing recombinant IFN-α2. Further, it is contemplated that the specific combinations of selected interferon species provided herein also will display greater efficacy than natural mixtures of multiple interferon compositions, particularly those containing at least about 48% by weight or more IFN-α2 protein species.

The antiviral compositions of this invention may be used in the substantial or total absence of IFN-α2 proteins. By the phrase "substantial absence of IFN-α2" is meant that a composition of this invention contains less than 10% by weight of an IFN-α2 species protein to the total weight of the pharmaceutical composition. Another desirable pharmaceutical composition of this invention contains less than 5% by weight of IFN-α2 to the total weight of the pharmaceutical composition. Still another desirable antiviral composition according to this invention contains no IFN-α2 protein species.

The selected proteins may also be employed in combination with amounts of other known antiviral proteins or therapeutics. In such compositions, the known antiviral agents may be used in less than the amounts conventionally required for therapeutic effectiveness. It is contemplated that the ability of an antiviral composition of this invention comprising one or a mixture of the above-listed selected high antiviral alpha interferon proteins when added to another antiviral agent may enhance the potency of the known antiviral agent, and enable the use of pharmaceutical compositions containing smaller amounts of that known antiviral agent for the indicated purposes for which it is presently used. The ability to use smaller amounts of such known antiviral proteins or chemical agents, will reduce the number and severity of side effects which accompany conventional antiviral therapy. In such a mixture, the selected proteins of the present compositions, used as an additive to the resulting pharmaceutical compositions, enhance the antiviral potency of the known antiviral agent, particularly with respect to retroviruses and hepatitis viruses.

Such conventionally employed antiviral agents to which the antiviral composition of this invention may be added include other proteins, such as cytokines including G-CSF, TNF, GM-CSF, M-CSF and other colony stimulating factors, interleukins such as IL-1 through IL-11; and other interferens, or chemical drugs, such as acyclovir, amantadine, idoxuridine, ribavirin, vidarabime, levamisole, trifluoridine, zidovudine and other known anti-viral agents. Particularly desirable known antiviral agents for use against HIV infections include AZT, ddI, ddC, IFN-α2a (Roferon® A), IFN-α2b (Intron® A), reverse transcriptase inhibitors such as L-697,661 (Merck), BHAP (bis(heteroaryl)-piperazine (Upjohn), Ti-Rg-587 (Nevirapine®, Boehringer-Ingelheim), d4T (stavudine®, Bristol-Myers Squibb), FLT (3-deoxy-3-fluorothymidine, American Cyanamid) and AzdU (Berlex Biosciences); R-82913 (TIBO derivative, RTase inhibitor, Janssen), Ro-24-7429 (TAT, transactivator of transcription inhibitor, Hoffman La-Roche), RO31-8959 (protease inhibitor, Hoffman La-Roche), rCD4 (Genentech), GLQ223 (compound Q, HIV replication inhibitor, GeneLabs), Hypericin (HIV replication inhibitor, VIMRX) and phosphonoformates. Particularly desirable antiviral agents for use against hepatitis infections include IFN-α2a, IFN-α2b and Ribavirin (Virazole®, ICN).

By the phrase "effective amount" with reference to the selected alpha interferon species consisting of α4a, α4b, α7a, α7b, α7c, α8a, α8b, α8c, α10a, α16, α17a, α17b, α17c, α17d, α21a, α21b and combinations thereof is meant at least 1%, and preferably at least 51%, by weight of each selected interferon species in the composition. By the terms "potency" or "antiviral potency" is meant that the antiviral composition of this invention has a greater antiviral activity than does an IFN-α2 protein species alone or known mixtures of alpha interferon alone. When used as an additive to a known antiviral agent, the term "antiviral potency" means that the resulting admixture has a greater antiviral activity than does the known antiviral agent, used alone.

The selected interferon protein species and mixtures noted particularly to be of use in the present invention include alpha interferon proteins defined by their amino acid sequences, which can be identified by the interferon gene sequences reported in the literature. The selected alpha interferon species useful in this invention were originally isolated from a purified mixture of natural human alpha interforth species and subunits, known as IFN-αn3a [International PCT Publication No. WO93/16107, published Aug. 19, 1993]. However, such selected species are readily available from other sources, including from recombinant or synthetic techniques, as well as isolation from other natural sources.

The selected alpha interferons useful in the antiviral compositions of this invention include the following IFN-α species and desirable combinations thereof characterized by high antiviral potency: α4a, α4b, α7a, α7b, α7c, α8a, α8b, α8c, α10a, α16, α17a, α17b, α17c, α17d, α21a and α21b. It is further contemplated that other alpha interferon species will, in the substantial absence of IFN-α2, demonstrate the same surprisingly therapeutically effective characteristics in contradiction to what has been noted in the art [see, e.g., Sperber et el, cited above).

It is presently preferable for use in this invention, that an antiviral composition according to this invention contain as its selected interferon protein species, IFN-α8b. Such a composition may contain an effective amount of IFN-α8b only or in admixture with IFN-α8 species, a and c. Another desirable composition of this invention includes at least one of IFN-α8a, 8b or 8c in admixture with less than about 10% by weight of IFN-α2. Still another desirable composition of this invention includes at least one of IFN-α8a, 8b, or 8c in the substantial or complete absence of IFN-α2. Other formulations are contemplated.

Still another desirable composition useful in this invention comprises one or a combination of α8a, α8b, α8c, with one or a combination of protein species selected from α17a, α17b, α17c, α17d, α21a, and α21b. As stated above, one or any combination of these proteins may provide a pharmaceutical composition in the complete or substantial absence of IFN-α2. Alternatively, another composition includes at least one of these above-identified selected highly antiviral species in admixture with less than 10% by weight IFN-α2. Still other combinations of these selected species are contemplated.

Still other desirable compositions of the present invention include the following mixtures. One such alpha interferon composition useful in the present invention comprises as its selected highly antiviral interferon species one or a combination of the species α4a, α4b, α16 in the total absence of IFN-α2. Another composition includes one or more of the selected highly antiviral species in admixture with less than about 10% by weight IFN-α2. Other specific combinations of these selected species are contemplated.

Another desirable composition useful in this invention comprises one or a combination of α7a, α7b, α7c, α17a, α17b, α17c, α17d, α21a, and α21b as the selected highly antiviral interferon species. As stated above, one or any combination of these proteins may provide a pharmaceutical composition in the complete or substantial absence of IFN-α2. Alternatively, another composition includes one or a combination of these above-identified selected species in admixture with less than 10% by weight IFN-α2. Still other combinations of these selected species are contemplated.

Yet another desirable composition useful in this invention comprises α10a as the selected highly antiviral interferon species. As stated above, this selected protein may provide a pharmaceutical composition in the complete or substantial absence of IFN-α2. Alternatively, another composition includes α10a as the selected species in admixture with less than 10% by weight IFN-α2. Another composition includes α10a and one or more of the selected species described in the several preceding examples in admixture with less than 10% by weight IFN-α2. This protein may be used alone in the composition of this invention, or combined with others of the above-listed highly antiviral proteins. Still other combinations of the selected species are contemplated.

Still an additional composition according to this invention contains all of the selected human alpha interferon protein species selected from α4a, α4b, α7a, α7b, α7c, α8a, α8b, α8c, α10a, α16, α17a, α17b, α17c, α17d, α21a, α21b in the absence of the following IFN-α species: α1, α5, α6, α10b, α13, α14, and α22. Another composition of the invention may contain the above ingredients in the presence of less than 10% by weight of IFN-α2 species proteins. Another formula involves the above composition characterized by the substantial absence of an IFN-α2 species protein.

For ease in discussion, the only preparative method for the individual alpha interferon proteins described in detail hereafter relates to isolation of these protein species from the natural, purified IFN-αn3a mixture and separation of the individual interferon species into the individual proteins or mixtures described above. In summary, the method exemplified for producing alpha interferon compositions of the present invention from the purified mixture IFN-αn3a involves both an induction process (described in detail in Example 1) and a purification process (described in Example 2) for IFN-αn3a, followed by characterization using reverse-phase high performance liquid chromatography (RP-HPLC) to separate selected interferon species from the IFN-αn3a according to their relative hydrophobicity (see Examples 3–6 below). However, it is anticipated that these selected proteins or mixtures thereof may also be prepared utilizing conventional recombinant techniques. The method of preparation of the alpha interferons for admixture into a pharmaceutical composition of this invention is not a limitation thereon.

Further, the anti-HIV activity of compositions containing the above selected interferon species proteins, in both the substantial absence of IFN-α2 species proteins and in the presence of amounts of IFN-α2 species less than 10% by weight of the total protein composition is demonstrated in comparison to IFN-α2 species proteins only in the assay of Example 7 below.

Both N-terminal and C-terminal sequences for the above-identified alpha interferon species have been identified in the IFN-αn3a composition, which has a hydrophobicity, measured on a RP-HPLC column, eluting between 40–60% acetonitrile as described in detail in Example 6, parts B and D.

The activity of the individual interferons or mixtures noted above has been determined in several biological assays. As described in detail in Example 4A, an antiviral assay [see, e.g., Linnette et al, *Cancer Therapy and Control,* 1:109–120 (1990)] was performed on human, bovine and rabbit cells. The antiviral specific activity of the interferon preparations described above on human and bovine cells in the assay ranges from 1 to $10 \times 10^8$ U/mg and is generally $\geq 2 \times 10^8$ U/mg. The interferon unit in this assay is defined as the reciprocal of the dilution at the 50% endpoint and is adjusted to the NIH reference standard (International Leukocyte Interferon Reference Preparation, Ga 23-902-530). The average antiviral specific activity on human HEp-2 cells for each species is about $\geq 2 \times 10^8$ U/mg.

Biological activity of these interferon compositions was also measured in an antiproliferative assay on human Daudi cells, as described in Example 4B below [see, e.g., Gillis et al, *J. Immunol.,* 12:2027 (1978)]. The specific activity ranges from about $5 \times 10^7$ U/mg to $5 \times 10^8$ U/mg for these compositions. The interferon unit in this assay is defined as the reciprocal of the dilution at 50% endpoint.

It has been demonstrated that the species IFN-α2, represented by species IFN-α2b and IFN-α2c, constitutes about 50% of the total IFN-αn3a protein mass, but is responsible for only about 25% of the total antiviral activity of the composition when the individual peaks of IFN-αn3a were separated into the non-α2 proteins or protein mixtures and measured separately in this assay on HEP-2 cells (see Table 5 below).

The purity of the IFN-αn3a composition from which the individual interferons or mixtures useful in this invention were originally obtained is measured both by sodium dodecylsulfate polyacrylamide gel electrophoresis (SDS-PAGE) and by Western blot procedures, as discussed in detail in Example 5 below.

Western blot analyses of the IFN-αn3a composition under non-reducing and reducing conditions, respectively, demonstrate that all of the interferon protein bands have an impurity level in unfractionated interferon of about 1% or less. Subsequent fractionation on RP-HPLC, shows no detectable impurity in any of the peaks.

Two-dimensional gel analyses for unfractionated IFN-αn3a show that there are multiple spots detected for all samples, all recognized by LIT-1 monoclonal antibody (see Example 5, part A, below) indicating that they are interferon proteins. The apparent molecular weight of the composition ranges between 16 to 27 kilodaltons as measured on SDS-PAGE gels. The IFN-αn3a composition is also characterized by an iscelectric point ranging between 5.0 to 7.5, and more preferably between 5.5 and 6.5. The number of spots and molecular weights for proteins in each of the peaks are summarized in Example 5, in Table 8 below.

The biochemical properties of the interferon compositions of this invention, e.g., determined by amino acid analyses, and amino and carboxyl terminal sequencing, are described in detail in Example 6. The amino and carboxyl terminal sequencing indicates that the interferon compositions contain intact interferon molecules, which consist of about 165–166 amino acid residues per molecule.

The alpha interferon antiviral compositions of this invention may be used alone to treat various viral diseases or used as additives to enhance the antiviral potency of other conventional antiviral agents, as described above. Preferably, the compositions of this invention either alone or as additives, are desirable for the treatment of retroviral diseases, including without limitation, HIV-1, HIV-2, HTLV I and HTLV II. The compositions of this invention are believed to have greater antiviral efficacy than the IFN-α2 containing compositions presently available for such treatment, particularly with respect to the treatment of HIV-I. Additionally, the compositions of this invention are also contemplated for the treatment of the various strains of hepatitis, including hepatitis A, B, C, D and E. The products may also be administered to treat other conditions susceptible to treatment with known alpha interferon compositions.

Pharmaceutical compositions of the invention, comprising an effective amount of the highly antiviral alpha interferon proteins selected from the group consisting of α4a, α4b, α7a, α7b, α7c, α8a, α8b, α8c, α10a, α16, α17a, α17b, α17c, α17d, α21a, α21b and/or mixtures thereof according to this invention, in a pharmaceutically acceptable carrier, can be administered to a patient having a disease or infection as described above. The therapeutic and pharmaceutical compositions of the present invention therefore comprise a therapeutically effective amount of at least one of the selected highly antiviral IFN-α protein species or combinations thereof as active ingredients. Such compositions may be in the substantial absence of IFN-α2. Optionally, such compositions may contain less than 10% by weight of IFN-α2. All such compositions are in admixture with a pharmaceutically acceptable carrier.

By "effective amount" is meant at least 1% by weight of each selected interferon species in the antiviral composition. More preferably, the "effective amount" is at least 5% by weight of each selected interferon species in the antiviral composition. Optionally such composition may also contain ≦10% by weight IFN-α2, or preferably no IFN-α2. When the antiviral compositions of this invention are employed as additives to other agents, the composition (whether a single highly antiviral protein or a mixture of proteins as described above) is desirably added to provide at least 1% by weight of the resulting total composition. More preferably, the antiviral compositions of this invention are used as additives to other antiviral agents to provide at least 5% by weight of the total resulting composition. Selected effective amounts may be optionally adjusted up or down depending on the desired increase in potency and/or the selected conventional antiviral agent added, and/or the condition being treated.

The pharmaceutical compositions may be utilized in conventional type formulations such as solutions, syrups, emulsions, injectables, tablets, capsules, topical formulations or suppositories. Suitable carriers are well known to those of skill in the art of pharmaceutical sciences (see, e.g., Remington's Practice of Pharmacy). Exemplary carriers include sterile saline and sugars such as xylitol, glycerol, lactose, and sucrose. Other carrier components include calcium phosphate, gelatin, dextrin, agar, cellulose, hydroxyethyl cellulose (for topical applications), petroleum jelly, polyethylene glycol, pectin, peanut oil, olive oil, sesame oil, squalene and water.

Additionally, the carrier or diluent may include a time delay material, such as glyceryl monostearate or glyceryl distearate alone or with a wax. Optionally, suitable chemical stabilizers may be used to improve the stability of the pharmaceutical preparation. Suitable chemical stabilizers are well known to those of skill in the art and include, for example, citric acid and other agents to adjust pH, chelating or sequestering agents, and antioxidants.

The formulations of the pharmaceutical composition may conveniently be presented in a unit dosage form and may be prepared by any of the conventional methods. Alternatively, the composition may be in a form adapted for slow release in vivo, as is known in the art. All methods include the step of bringing into association the active ingredient(s) with the carrier which may constitute one or more accessory ingredients.

The amount of the composition which will be effective in the treatment of a particular disorder or condition will depend on the nature of the disorder or condition, and can be determined by standard clinical techniques. However, it is contemplated that compositions of this invention may employ lower dosages of IFN-α2 proteins than presently available interferon preparations.

Methods of introduction include, but are not limited to, intralesional, intradermal, intramuscular, intraperitoneal, intravenous, subcutaneous, topical, oral, and intranasal. Further, it may be desirable to administer the pharmaceutical compositions of the invention locally to the area in need of treatment. This may be achieved by methods including, but not limited to, local infusion during surgery, by injection, by means of a catheter, or by means of an implant, said implant being of a porous, non-porous, or gelatinous material, including membranes, such as sialastic membranes, or fibers.

The invention also provides for pharmaceutical compositions administered via liposomes, microparticles, or microcapsules. In various embodiments of the invention, it may be useful to use such compositions to achieve sustained release of the substances. In a specific embodiment, it may be desirable to utilize liposomes targeted via antibodies to specific identifiable tumor antigens (e.g., cell surface antigens selective for neuroblastoma or SCLC) [Leonetti et al, Proc. Natl. Acad. Sci. USA, 87:2448–2451 (1990); Renneisen et al, J. Biol. Chem., 265:16337–16342 (1990)].

The alpha interferon antiviral compositions of the present invention may also be employed in accordance with the methods and compositions of this invention, alone or in combination with other therapeutic or diagnostic agents useful in the direct or adjunctive treatment of hepatitis and retroviral infections. It is contemplated that these compositions may be used in combination with other agents, e.g., antimetabolites, alkylating agents, vinca alkaloids, antineoplastic antibiotics, platinum derivatives, substituted ureas, adrenocorticosteroids, or antibodies.

The dosage regimen involved in administering an effective amount of the compositions of this invention in a method for treating the above-described conditions will be determined by the attending physician considering various factors which modify the action of drugs, e.g. the condition, body weight, sex and diet of the patient, time of administration and other clinical factors. The dosage of the compositions of the invention used to treat the specific disease conditions described herein may be varied depending on the particular disease and the stage of the disease. For example, for treatment of AIDS or other retroviral infections requiring aggressive treatment, an appropriate dose may be considerably less than the 30–36 MU indicated for presently approved recombinant alpha interferons which contain IFN-α2 proteins due to the potency of the compositions of this invention. More specifically, it is anticipated that the dosage of IFN-α protein compositions of this invention for such infections would range between about 0.1 million units to 10 million units per dose.

Dosages may generally be administered three times a week. Other dosages and regimens may be determined by one of skill in the art with the application of routine skill.

However, in one embodiment of this invention, namely the treatment of a retroviral infection, e.g., HIV I, a composition of this invention is administered as an intramuscular or subcutaneous injection at a dosage of about 0.5 MU or less, three times a week for three months. As another example, for the treatment of hepatitis (strains A through E), a composition of this invention is administered as an intramuscular or subcutaneous injection at a dosage of about 1 MU or less, three times a week for six months.

When the compositions of this invention are added to other antiviral agents as an additive, the dosages of the resulting compositions are equal to or less than the currently effective dosages for the antiviral agent alone.

In addition to treating the mammalian disorders described hereinabove, the compositions of this invention may be utilized for veterinary purposes in the treatment of viral or other diseases that afflict horses, swine, cattle, canines, felines and fowl, for example. These disorders may be treated using quantities of the compound that may be used in treating the mammalian disorders described hereinabove.

The following examples are for illustrative purposes only, and should not be construed as limiting this invention in any way.

EXAMPLE 1

METHOD OF PRODUCING IFN-αn3a—INDUCTION

This example provides one specific protocol for the induction process used in the production of IFN-αn3a. Additional information on alternative modifications of this procedure are found in published International PCT Publication No. WO93/16107. However, as noted, this method is only provided for exemplary purposes and is not essential to the practice of this invention, as any known means for obtaining the selected interferon proteins may be employed.

For the preparation of buffy coats, 500 units of human PBLs are obtained from FDA-approved blood centers. Red blood cells are then lysed using an ammonium chloride treatment (0.83%) according to Cantell et al., (1981), cited above.

Ammonium chloride-treated buffy coats are resuspended in 1×Eagle's MEM containing Earle's salts (Gibco 410–1500), L-glutamine, non-essential amino acids, 4.46 mg/ml Tricine (Aldrich), pH 7.4, 2.2 mg/ml sodium bicarbonate (Fisher), 24 μg/ml of Neomycin Sulfate, and 0.4 mg/ml of human agamma serum (NABI).

Leukocytes ($10^7$ cells/ml) are suspended in 1×MEM and 20 units/ml of crude alpha interferon are added as a primer. The crude alpha interferon is the product resulting from the induction steps described herein, without purification, adjusted with HCl to pH 2 for five days to inactivate any adventitious agents or potential viral contaminants.

This suspension is incubated in 6 liter sterile glass flasks. Leukocytes are primed for 3 hours at 36° C. followed by addition of the Sendai virus (Cantell strain from SPAFAS; Storr, CT) at a final concentration of 150 HA units/ml.

After 1 hour incubation to allow virus attachment, leukocytes are diluted to $4 \times 10^6$ cells/ml (2.5 fold) with the same medium containing agamma serum, sodium bicarbonate and no primer. This is followed by an additional 15 hours incubation at 36° C. Cells and debris are then removed by centrifugation at 2,500 rpm (Beckman model J6-B) and crude interferon titers are then assayed by IRMA or CPE assays as previously described above.

EXAMPLE 2

METHOD OF PRODUCING IFN-αn3a—PURIFICATION

This example provides one specific protocol for the purification process used in the production of IFN-αn3a. Additional information on alternative modifications of this procedure are found in the above-cited published PCT application. However, for the reasons noted above, this method is only provided for exemplary purposes and is not essential to the practice of this invention.

All purification steps are performed at 2°–8° C. unless otherwise indicated.

A. Collection/Concentration of Crude interferon

After incubation for 15–20 hours, the leukocytes are removed from the induction cultures of Example 1 by centrifugation at approximately 2,900× g for 15–20 minutes. The supernatant (crude interferon solution) is reserved and the leukocytes discarded. If not to be processed immediately, the supernatant is stored in sterilized containers at 4° C.

The crude interferon solution is concentrated at 50 fold, using a tangential flow filter system with a nominal molecular weight cut off of 10,000. The concentrated interferon is centrifuged at approximately 9,000× g for about 30 minutes. The concentrated interferon can be stored at –70° C.,

B. Affinity Purification

1. Preparation of Chromatography Columns

This purification method uses monoclonal antibody specific to human alpha interferons, e.g. NK2 produced by Celltech Limited (Slough, England). The monoclonal antibody is coupled to CNBr activated Sepharose-4B (e.g., Resolute NK2) and stored at 4° C. The size of the affinity column is dependent on the binding capacity of the affinity gel for interferon, which is determined on each preparation. Columns are prepared by pouring an appropriate amount of Sepharose-antibody gel into a suitable glass column. The monoclonal antibody column is washed with approximately 5 column volumes of phosphate buffered saline followed by washing with 3 column volumes of a solution containing 0.1M citric acid and 0.3M sodium chloride at pH 2. The pH of the column is then neutralized to 7.4 by washing with 3 column volumes of phosphate buffered saline (PBS). This pro-wash cycle may be repeated for a couple more times.

2. Preparation of Concentrated Crude IFN

The concentrated crude interferon is clarified by centrifugation at approximately 17,700× g for 60 minutes and is filtered utilizing appropriate cartridge 0.22 or 0.45 micron filters prior to loading onto monoclonal antibody column.

3. Affinity Purification

Approximately 150 million units of crude filtered interferon is loaded per ml of affinity gel. Interferon units are determined by IRMA (Celltech Ltd.). The column is washed with approximately 1.5 column volumes of phosphate buffered saline followed by 10 column volumes of a 20 mM phosphate buffer (pH 7.4) containing 50% (v/v) ethylene glycol and 1.5M sodium chloride. The washes are completed with a final 10–30 column volumes of phosphate buffered saline. The interferon is eluted from the affinity column with a solution containing 0.1M citric acid and 0.3M sodium chloride (pH 2).

4. Regeneration of Affinity Column

The monoclonal antibody column is washed with 3–5 column volumes of phosphate buffered saline until the pH of the eluate is neutral. For storage of column, the column is washed with 3–5 column volumes of phosphate buffered saline containing 0.1% sodium azide.

C. Acid Incubation and Neutralization

The eluted interferon solution (about pH 2) from the monoclonal affinity column is incubated at 4° C. for a minimum of 5 days. This acid incubation step is necessary to inactivate any potential adventitious agents, such as HIV-1. After 5 days storage period the pH of the solution is adjusted to 7.4 with 1.0M Tris. HCl (hydroxymethylaminomethane). The interferon protein in the solution is concentrated to approximately 1–3 mg/ml.

D. Gel Filtration

The preparative grade Superose 12 beads (Pharmacia, Piscataway, N.J.) are used for the gel filtration chromatography. Concentrated interferon in 5% of the column volume is loaded and eluted with phosphate buffered saline. All fractions constituting the main peak containing interferon are aseptically pooled. The purified interferon is filtered using a 0.2 micrometer or smaller low binding filter and stored at –70° C.

E. Results

Results from a typical purification procedure are shown in Table 2 indicating purification step (Purifn Step), total volume and mass of proteins, total activity, which is indicated as the number in the column multiplied by $10^9$ Units, percentage yield as determined by the total IRMA units recovered at each step, specific activity (Spec. Actvy) measured in million units (MU)/mg, and fold purification (Purifn. Fold). Interferon activity is determined by immunoradiometric assay [Celltech, Ltd.] which uses radiolabeled NK2 as the detecting antibody.

Peaks 2 and 4 contain small quantities of material. Peak 2 was not further characterized for amino acid composition and carbohydrate content. Peak 4 was not further characterized for amino-sugar content following HCl hydrolysis.

After lyophilization, the interferon in each peak was reconstituted in 25 mM Tris-HCl buffer at pH 7.0. The reconstituted material was then pooled accordingly from all column runs for subsequent analyses.

TABLE 2

| Purifn Step | Protein | | Interferon Activity | | | Purifn Fold |
|---|---|---|---|---|---|---|
| | Total | | Total | | Spec. | |
| | Vol (L) | Mass (mg) | Act'y (× $10^9$ IU) | % Yield | Act'y (MU/mg) | |
| Crude IFN | 212.4 | $8.5 \times 10^4$ | 4.6 | 100 | 0.054 | 1 |
| Concentration | 5.15 | $7.1 \times 10^2$ | 4.5 | 99 | 0.064 | 1 |
| NK2 Affin'y Chromatog'y | 0.073 | 9.4 | 4.0 | 87 | 430 | 7,990 |
| Neutraliz'n Concentra'n | 0.0073 | 7.3 | 3.4 | 74 | 470 | 8,740 |
| Superose Chromatog'y | 0.045 | 4.8 | 3.2 | 70 | 660 | 12,200 |

EXAMPLE 3

SEPARATING IFN-α SPECIES BY RP-HPLC

In this example alpha interferon species in the composition are separated according to their relative hydrophobicity using RP-HPLC [Janssen et al., *J. Chromatoaraphic Sci.*, 22:234 (1984); Stone et al., *J. Chrom.* 359:203 (1986)]. The separation was achieved by increasing acetonitrile concentration. The least hydrophobic interferon species eluted as early peaks and the most hydrophobic interferon species eluted later.

The typical RP-HPLC profile has been obtained from the semi-preparative column runs, as shown in FIG. 1A, as follows. Approximately 1–2 mg of purified interferon IFN-αn3a was fractionated on a semi-preparative Vydac C4 reverse phase HPLC column (10×250 mm). The linear elution gradient used for the semi-preparative C$_4$RP-HPLC is shown in Table 3, with buffers as follows: A:90% H$_2$O/10% ACN/0.1% TFA v/v/w; and B:90% ACN/10% H$_2$O/0.1 TFA v/v/w.

TABLE 3

| TIME | FLOW RATE | % A | % B |
|---|---|---|---|
| initial | 5.0 ml/min | 95 | 5 |
| 15 min | 5.0 ml/min | 60 | 40 |
| 59 min | 5.0 ml/min | 50 | 50 |
| 60 min | 5.0 ml/min | 10 | 90 |
| 65 min | 5.0 ml/min | 10 | 90 |
| 66 min | 5.0 ml/min | 95 | 5 |
| 76 min | 5.0 ml/min | 95 | 5 |
| 79 min | 0.04 ml/min | 95 | 5 |

The purified interferon was fractionated into 7 peaks, i.e., Peaks 1.1, 1.2, 2, 3, 4, 5 and 6. The first peak resolved into two partially overlapping peaks, i.e. 1.1 and 1.2. These two peaks were characterized separately in all analyses. The proteins in each peak were collected individually.

The relative proportion of each peak from a typical RP-HPLC profile vs. the total unfractionated IFN αn3a is shown in Table 5 discussed in more detail below (% of protein and activity).

EXAMPLE 4

BIOLOGICAL ASSAYS

A. Antiviral Assay:

An antiviral assay was performed using three different cell lines: 1) human HEp-2 [ATCC CCL 23], 2) bovine MDBK [ATCC CRL 6071], and 3) rabbit RK-13 [ATCC CCL 37] cells. The interferon was serially two-fold diluted in 96-well plates, followed by addition of 30,000 cells/well. After an overnight incubation, cells were infected with VSV (Indiana strain ATCC #VR-158), followed by an additional overnight incubation. Cytopathic effect (CPE) is checked microscopically on virus control, cell control and cells which received standard interferon. Cells were stained with crystal violet when the wells containing standard interferon showed proper CPE. For all samples, 50% cytopathic effect is measured visually, and interferon titer is calculated by comparison to the laboratory standards which had been previously standardized against the NIH interferon reference standard (Ga 23-902-530). The results are reported in Table 4 below.

B. Antioroliferative Assay

Antiproliferative assay is measured in human lymphoblastoid Daudi cells. Interferons are serially 5 fold diluted in 96-well plates (100 μl /well) followed by addition of $10^4$ Daudi cells/well (in 100 μl). After 40 hours incubation, cells are treated with 1.5 μCi/well (in 25 μl) of $^3$H-thymidine for 7 hrs. Thymidine uptake is measured by harvesting and washing cells with water on glass fiber filters followed by measurement of incorporated radioactivity using a scintillation counter. Again, titers are calculated and corrected against laboratory standards.

C. Assay Results

The antiviral and anti-proliferative characteristics of unfractionated IFN-αn3a and the RP-HPLC-separated interferon mixtures of the present invention are presented below in Table 4.

TABLE 4

Specific Activities of IFN-αn3a RP-HPLC Peaks

| | MU/mg IFN | | | |
|---|---|---|---|---|
| | CPE | | | AP |
| Peak # | HEp-2 | MDBK | RK-13 | Daudi |
| 1.1 [α2 (b/c)] | 252.0 | 262.9 | 0.08 | 86.9 |
| 1.2 [α2 (b/c)] | 195.6 | 265.0 | 0.17 | 109.4 |
| 2 [α4 (a/b); α16] | 269.8 | 278.1 | 0.77 | 127.5 |
| 3 [α10a] | 377.3 | 316.8 | 7.09 | 175.7 |
| 4 [α8 (a/b/c); α21 (a/b); α17 (a/b/c/d)] | 589.9 | 345.1 | 2.63 | 216.4 |
| 5 [α21 (a/b); α7 (a/b/c) α17 (a/b/c/d)] | 298.6 | 362.7 | 1.56 | 205.5 |
| 6 [α8 (a/b/c)] | 884.1 | 447.7 | 0.59 | 237.9 |
| Unfractionated IFN-αn3a | 502.0 | 426.7 | 1.94 | 149.2 |

The specific biological activity is presented as the number of biological units per mg of the total protein present. The data in Table 4 show that the specific CPE activities on human HEp-2 and bovine MDBK cells are similar in each separated interferon preparation. The specific antiproliferative activity on Daudi cells is approximately 2 fold less than the antiviral activities in each separated preparation. When the interferon was assayed on rabbit kidney cells (RK-13), some CPE activity was detected. The specific activity is at least 100 to 1000 fold lower than that on human or bovine cells. Interestingly, the interferon α10a has the highest specific activity on RK-13 cells. The data presented in Table 4 also demonstrate that the peaks containing substantial amounts of IFN-α2 contained the lowest specific activities on HEp-2, MDBK and Daudi cells.

The contribution of each peak in the biological activity on HEP-2 cells is summarized in Table 5.

TABLE 5

Distribution in RP-HPLC Peaks

| Peak # | Protein % | Activity % |
|---|---|---|
| Total (unfrac.) | 100 | 100 |
| 1 (1.1 + 1.2) | 48.9 | 25 |
| 2 | 4.3 | 4.6 |
| 3 | 15.1 | 7.7 |
| 4 | 4.6 | 5.2 |
| 5 | 9.7 | 7.5 |
| 6 | 17.4 | 49 |

When peak 1 (peaks 1.1 and 1.2 taken as a single peak) was tested in this assay, it constituted only about 25% of the total antiviral activity of the IFN-αn3a composition, even though it was almost half the protein content of the IFN α-n3a mixture. The later eluting interferon preparation containing α8 species only (peak 6) contains the highest specific activities. In fact, when the specific activity is plotted against the percent of acetonitrile in the elution gradient, a direct correlation is seen between the increase in specific activity and the relative increase in hydrophobicity of the alpha interferon protein. The more hydrophobic the interferon is, the higher specific activity it has. It is contemplated that the more hydrophobic interferon species, like α8, bind to the interferon receptor(s) with a higher affinity, or bind to a separate class of interferon receptor(s) which may result in higher response or initiate cellular events more efficiently and therefor show a higher specific activity.

EXAMPLE 5

PHYSICAL PROPERTIES OF IFN PROTEINS

The interferon proteins in the seven interferon preparations fractionated on reverse phase HPLC were characterized by SDS-PAGE.

A. One dimensional SDS-PAGE

1. Methods

One dimensional SDS polyacrylamide gel electrophoresis (SDS-PAGE) analyses were performed using procedures similar to those described by Laemmli, Nature, 277:680 (1979). The IFNs were analyzed in 14.5% SDS-PAGE under both reducing and non-reducing conditions. The protein bands were visualized by Coomassie blue staining. A Western blot of duplicated SDS gel was immunostained with LIT-1 murine monoclonal antibody specific to human IFN alpha and developed as described [Towbin et al. Proc. Natl. Acad Sci (USA) 76:4350 (1979); and Haid et al., Meth. Enzymol., 96:192 (1983)].

2. Results

The data for non-reducing and reducing SDS-PAGE profiles are summarized below, in Table 6 and 7, respectively.

TABLE 6

SDS-PAGE (non-reduced)
Relative Molecular Weights and Area Percentages

| | Relative Area Percent (%) | | | | | | | |
|---|---|---|---|---|---|---|---|---|
| Molecular Weight (KD) | Unfract'd IFN | α2 | α2 | α4/α16 | α10a | α8/ α21/ α17/ | α17/ α21/ α7 | α8 |
| 19.3 | 17.1 | — | — | 17.8 | — | 36.5 | 1.6 | 29.8 |
| 19.0 | 27.4 | — | — | — | — | — | 1.2 | 70.2 |
| 18.5 | 26.3 | 93.8 | 93.1 | — | — | — | — | — |
| 18.0 | 6.5 | 6.2 | 4.8 | — | — | — | — | — |
| 17.8 | — | — | 2.1 | 18.3 | 17.1 | 52.0 | 21.0 | — |
| 17.7 | 19.2 | — | — | — | 82.9 | — | — | — |
| 17.5 | 3.4 | — | — | 57.2 | — | 11.6 | 76.2 | — |
| 17.2 | — | — | — | 6.8 | — | — | — | — |

TABLE 7

SDS-PAGE (Reduced)
Relative Molecular Weights and Area Percentages

| | Relative Area Percent (%) | | | | | | | |
|---|---|---|---|---|---|---|---|---|
| | RP-HPLC peaks of Interferon | | | | | | | |
| Molecular Weight (KD) | Unfract'd IFN | α2 | α2 | α4/α16 | α10a | α8/ α21/ α17/ | α17/ α21/ α7 | α8 |
| 27.7 | — | — | — | — | — | — | 2.3 | — |
| 27.5 | — | — | — | 0.9 | — | — | — | — |
| 27.0 | 23.8 | — | — | — | — | 34.3 | — | 100.0 |
| 22.3 | — | — | — | — | 16.8 | — | — | — |
| 21.7 | 58.1 | — | — | — | 83.2 | 17.6 | — | — |
| 21.5 | — | 92.4 | 80.8 | 73.4 | — | — | 40.8 | — |
| 20.8 | 9.4 | 7.6 | 13.2 | — | — | 41.7 | — | — |
| 20.0 | 4.1 | — | 2.8 | — | — | 6.4 | 56.9 | — |
| 19.4 | 1.3 | — | 3.2 | — | — | — | — | — |
| 19.0 | 1.5 | — | — | — | — | — | — | — |

TABLE 7-continued

SDS-PAGE (Reduced)
Relative Molecular Weights and Area Percentages

| Molecular Weight (KD) | Relative Area Percent (%) | | | | | | | |
|---|---|---|---|---|---|---|---|---|
| | RP-HPLC peaks of Interferon | | | | | | | |
| | Unfract'd IFN | α2 | α2 | α4/α16 | α10a | α8/ α21/ α17/ | α17/ α21/ α7 | α8 |
| 18.6 | 1.7 | — | — | 22.4 | — | — | — | — |
| 13.0 | — | — | — | 3.3 | — | — | — | — |

The data in Tables 6 and 7 demonstrate heterogeneity (i.e. there is more than one protein band) in most of the separated interferon preparations. However, note that under reducing conditions only, one interferon preparation (peak 6) contains the single protein band α8 by this method.

The relative number of interferon protein bands in each interferon preparation was determined by laser densitometry. The relative molecular weights were calculated by comparing with the molecular weight markers.

The results from Western blot analyses for the non-reducing and reducing conditions, respectively show that every protein band detectable by Coomassie blue staining was recognized by the LIT-1 monoclonal antibody. This demonstrates that all protein bands in each interferon preparation are identified as human alpha interferons. The impurity level in unfractionated interferon is approximately 1%. After fractionation on RP-HPLC, this low level of impurity was not detectable in any of the interferon preparations.

Characterization continued with two-dimensional gel analysis.

B. Two-Dimensional SDS-PAGE

1. Methods

Two dimensional gel electrophoresis includes the isoelectric focusing in the first dimension and SDS-PAGE in the second dimension. For the first dimensional analysis, 5–10 μg of interferon from each RP-HPLC peak was loaded onto an acrylamide/urea gel casted in a glass tube (2×180 mm). The tube gel is run at constant voltage of 400 volts for 16 hours followed by 800 volts for 1 hour. The ampholines (Millipore) with a pH range between 3 and 10 are used for isoelectric focusing analysis. The tubular gel was then extruded from the glass tube, equilibrated in SDS sample buffer and layered on a 15% SDS-polyacrylamide slab gel for the second dimensional analysis. The SDS-PAGE is run in a Tris/glycine buffer at pH 8.3 at constant current of 35 mA. The proteins in the 2-D gels were visualized by silver staining. Interferon protein was identified by immunostaining with LIT-1 monoclonal antibody.

2. Results

The results of the two-dimensional gel analyses for unfractionated IFN-αn3a and the protein in each RP-HPLC interferon preparation or separated peak show that there are multiple spots detected for all samples. The unfractionated IFN-αn3a has approximately 30 spots by 2-D gel analysis. All spots are recognized by LIT-1 monoclonal antibody, indicating that they are indeed interferon proteins. The number of spots and molecular weights for proteins in each of the interferon preparations are summarized in Table 8 below. The isoelectric points for all interferon proteins in IFN-αn3a are within the pI range of 5.0 to 7.5.

TABLE 8

Analysis of 2-D Gel Profiles

| Peak # | Number of Spots* | Molecular Weight (Kdal) |
|---|---|---|
| IFN** | 30–35 | 17.7–27.8 |
| 1.1 | 8–10 | 20.6–22.8 |
| 1.2 | 8–11 | 18.9–22.8 |
| 2 | 3–4 | 22.8 |
| 3 | 4–5 | 21.9–22.8 |
| 4 | 6–9 | 21.9–27.8 |
| 5 | 5–7 | 21.9–22.8 |
| 6 | 1 (smear) | 27.8 |

*Stained with Silver Stain and Immunostain
**Unfractionated

The 2-D gel profiles for interferon preparations containing α2 (peaks 1.1 and 1.2) appear to be very similar. There is little difference in molecular size and charge. They may elute separately on RP-HPLC due to some non-charge related modifications of the proteins. The 2-D gels for the rest of interferon preparations are quite different from each other. The profile for each interferon preparation has its own characteristics. The multiple spots present in each interferon preparation indicate the heterogeneous population of proteins. This heterogeneity may be due to differences in translation and/or post-translational modifications of the proteins.

EXAMPLE 6

BIOCHEMICAL PROPERTIES OF INTERFERON PREPARATIONS

A. Amino Acid Composition

Interferon protein was hydrolyzed in 6N HCl at 104° C. for 24 hours in a Pico-Tag heating block. The hydrolysates were dried under vacuum and derivatized with 10% phenylisothiocyanate (PITC) in a solution of 70% ethanol, 10% water and 10% triethylamine. The resulting phenylthiocyanate (PTC) amino acids were separated by Pico-Tag C18 HPLC column. Elution of the PTC-amino acids was carried out with a 0–60% linear gradient of acetonitrile in water containing 140 mM sodium acetate (pH 6.4) and 0.05% triethylamine. The absorbance of PTC amino acids was measured at 269 nm. Absorbance data from each analysis were digitally acquired and stored in a microcomputer. The amino acid residues, cysteine and tryptophan, are altered during hydrolysis, and consequently do not give a signal corresponding to their intact standards. Hence, these two residues are not included in the analysis. The data were then analyzed for amino acid identification and quantitation using the Water's Expert software package.

The results from the amino acid composition analyses for alpha interferon and individual RP-HPLC interferon preparations are presented in Table 9. Table 9 shows that in general the amino acid compositions of separated interferon preparations are similar to that of unfractionated interferon and to those species recognized by NK-2 monoclonal antibody. When the composition of each interferon preparation (or peak) is compared with the theoretical composition of specific species identified by N-terminal sequencing there is agreement within ±1 residue.

TABLE 9

Theoretical Amino Acid Composition of IFN-α Species

| Amino Acid Residues | IFN α2 | | | INF α8 | | | IFN α10 | | IFN α4 | | IFN α17 | | | | IFN α7 | | | IFN α16 | IFN α21 | |
|---|---|---|---|---|---|---|---|---|---|---|---|---|---|---|---|---|---|---|---|---|
| | 2a | 2b | 2c | 8a | 8b | 8c | 10a | 10b | 4a | 4b | 17a | 17b | 17c | 17d | 7a | 7b | 7c | α16 | 21a | 21b |
| Asx | 12 | 12 | 12 | 16 | 15 | 16 | 14 | 14 | 13 | 13 | 14 | 14 | 14 | 14 | 12 | 12 | 12 | 14 | 13 | 13 |
| Glx | 26 | 26 | 26 | 28 | 28 | 27 | 29 | 29 | 29 | 28 | 29 | 29 | 29 | 29 | 29 | 30 | 29 | 26 | 29 | 29 |
| Ser | 14 | 14 | 14 | 15 | 16 | 15 | 14 | 13 | 14 | 14 | 154 | 14 | 14 | 13 | 13 | 13 | 13 | 13 | 14 | 14 |
| Gly | 5 | 5 | 5 | 2 | 2 | 2 | 5 | 5 | 5 | 5 | 5 | 5 | 5 | 5 | 4 | 3 | 4 | 4 | 5 | 5 |
| His | 3 | 3 | 2 | 3 | 3 | 3 | 3 | 3 | 5 | 5 | 2 | 3 | 3 | 3 | 4 | 4 | 4 | 4 | 3 | 3 |
| Arg | 9 | 10 | 11 | 10 | 10 | 9 | 13 | 13 | 11 | 11 | 10 | 10 | 11 | 11 | 12 | 13 | 12 | 15 | 10 | 10 |
| Thr | 11 | 11 | 11 | 6 | 6 | 6 | 7 | 8 | 8 | 9 | 9 | 9 | 9 | 9 | 8 | 8 | 9 | 8 | 8 | 8 |
| Ala | 8 | 8 | 8 | 9 | 9 | 9 | 9 | 9 | 10 | 9 | 9 | 9 | 9 | 9 | 9 | 9 | 9 | 8 | 9 | 9 |
| Pro | 5 | 5 | 5 | 4 | 4 | 4 | 5 | 5 | 4 | 4 | 6 | 5 | 5 | 6 | 5 | 5 | 5 | 4 | 5 | 5 |
| Tyr | 5 | 5 | 5 | 5 | 5 | 5 | 4 | 4 | 4 | 4 | 4 | 4 | 4 | 4 | 4 | 4 | 4 | 5 | 3 | 3 |
| Val | 7 | 7 | 7 | 7 | 7 | 7 | 7 | 7 | 7 | 8 | 6 | 6 | 6 | 6 | 7 | 7 | 7 | 9 | 8 | 8 |
| Met | 5 | 5 | 5 | 4 | 5 | 5 | 4 | 4 | 4 | 4 | 5 | 5 | 5 | 5 | 5 | 5 | 4 | 6 | 5 | 4 |
| Cys | 4 | 4 | 4 | 4 | 4 | 4 | 4 | 4 | 4 | 4 | 4 | 4 | 4 | 4 | 4 | 4 | 4 | 4 | 4 | 4 |
| Ile | 8 | 8 | 8 | 10 | 10 | 10 | 10 | 11 | 8 | 8 | | 9 | 8 | 8 | 8 | 8 | 8 | 6 | 9 | 9 |
| Leu | 21 | 21 | 21 | 22 | 22 | 21 | 20 | 19 | 20 | 20 | 21 | 21 | 21 | 21 | 19 | 19 | 19 | 20 | 18 | 19 |
| Phe | 10 | 10 | 10 | 10 | 10 | 10 | 9 | 9 | 10 | 10 | 9 | 9 | 9 | 9 | 12 | 12 | 12 | 9 | 11 | 11 |
| Lys | 11 | 10 | 10 | 10 | 10 | 8 | 7 | 7 | 8 | 8 | 8 | 8 | 8 | 8 | 9 | 8 | 9 | 8 | 10 | 10 |
| Trp | 2 | 2 | 2 | 1 | 1 | 1 | 2 | 2 | 2 | 2 | 2 | 2 | 2 | 2 | 2 | 2 | 2 | 3 | 2 | 2 |

Measured Amino Acid Composition of IFN-αn3a

| Col. # | Unfrac. IFN α-n3a | RP-HPLC Peaks | | | | | | |
|---|---|---|---|---|---|---|---|---|
| | | 1.1 | 1.2 | 2 | 3 | 4 | 5 | 6 |
| 1 | 12 | 11.6 | 10.3 | NA | 13.4 | 13.7 | 7.7 | 14.8 |
| 2 | 25.2 | 23.5 | 22.1 | NA | 27.8 | 23.9 | 24.2 | 27.8 |
| 3 | 14.1 | 14.7 | 14.7 | NA | 13.0 | 14.6 | 15.4 | 14.2 |
| 4 | 4.7 | 5.5 | 5.7 | NA | 5.3 | 4.2 | ND | 2.5 |
| 5 | 2.8 | 3.1 | 2.6 | NA | 2.7 | 2.8 | 3.0 | 3.0 |
| 6 | 10.4 | 10.4 | 10.6 | NA | 11.9 | 11.0 | 11.3 | 10.2 |
| 7 | 8.9 | 10.7 | 10.7 | NA | 6.3 | 6.8 | 8.9 | 5.6 |
| 8 | 9.3 | 8.8 | 8.7 | NA | 8.7 | 8.5 | 8.7 | .0 |
| 9 | 9.1 | 4.9 | 6.0 | NA | 8.3 | ND | 4.5 | 5.0 |
| 10 | 4.4 | 5.0 | 5.8 | NA | 4.0 | 4.0 | 5.1 | 5.4 |
| 11 | 6.0 | 6.1 | 6.2 | NA | 5.4 | 5.4 | 5.5 | 5.4 |
| 12 | 4.8 | 5.4 | 5.5 | NA | 3.9 | 5.0 | 5.4 | 5.2 |
| 13 | ND | ND | ND | NA | ND | ND | ND | ND |
| 14 | 7.6 | 7.7 | 8.7 | NA | 8.4 | 7.8 | 9.8 | 9.5 |
| 15 | 19.5 | 16.8 | 16.8 | NA | 20.3 | 23.8 | 18.3 | 17.7 |
| 16 | 9.6 | 10.7 | 11.0 | NA | 9.2 | 10.4 | 12.1 | 10.4 |
| 17 | 9.1 | 11.0 | 11.1 | NA | 7.3 | 9.2 | 9.9 | 10.4 |
| 18 | ND | ND | ND | ND | ND | ND | ND | ND |

B. N-Terminal Amino Acid Sequence

The procedures used for N-terminal amino acid sequence analyses are similar to those previously described. [Edman, Acta Chem. Scant. 4:283 (1950); Edman et al. Eur. J. Biochem, 1:80 (1967)].

For each RP-HPLC peak, approximately 500 pmoles of protein were loaded on a pre-cycled filter and sequenced for 30–35 cycles. The sequencing was performed on an Applied Biosystems ABI-470A sequencer equipped with an on-line phenylhydantion (PTH) amino acid analyzer. The sequencing procedure in this instrument is based on Edman degradation.

N-terminal sequencing based on Edman degradation is very effective in identifying and quantitating residues in relatively short peptide sequences (,i.e. <20). However, for long peptide sequences (i.e. >30) the identification of residues closer to the C-terminus of the protein or polypeptide becomes ambiguous. This increase in ambiguity is due to the repetitive yield, which is generally less than 95% and therefore, leads to a cumulative loss of signal for each additional cycle.

For this reason, proteins in peaks 1.1 and 1.2 were cleaved at methionine residues with CNBr, and the resulting fragments were separated by RP-HPLC and sequenced. By this method, the identity of the IFN species found in peaks 1.1 and 1.2 were determined with great accuracy. The cleavage was performed by first dissolving the alpha interferon protein in 70% formic acid and then adding CNBr to a concentration of 1M and incubating at 4° C. for 24 hours. The cleavage reaction was terminated by lyophilization in a speed-vac (Savant, Long Island, N.Y.), thus removing all solvents including CNBr from the reaction tube. The dried CNBr fragments were dissolved in 50% TFA and injected onto a C4 column (0.4×25 cm, Vydac, Hesperin, Calif.). Elution of the fragments was accomplished by a multi step gradient of 0.1% TFA/$H_2O$ (solvent A) and 0.1% TFA/acetonitrile (solvent B). The multi step linear gradients used are as follows: 1) 0% to 50% solvent B in 50 minutes, 2)50% to 80% solvent B in 15 minutes, and 3) 80% to 90% solvent B in 2 minutes. Detection of the eluting fragments was accomplished by monitoring absorbance at 214 nm. The resolved fragments were sequenced as indicated above or analyzed further. For the latter case, CNBr fragment 3 was resuspended in 50 mM ammonium bicarbonate (Sigma) and digested with trypsin (US Biochemicals) at a weight ratio of 1:20 (enzyme to substrate) for 16–18 hours at 37 degrees C. The resulting digestion product was chromatographed on a C18 column (25×0.4 cm, Vydac) with a gradient of 0.1% TFA/water (solvent A) and 0.1% TFA/acetonitrile (solvent B). The following gradient program was used: isocratic at 100% solvent A for 2 minutes, 0 to 75% B in 75 minutes, 75 to 90% B in 3 minutes and isocratic at 90% B for 5 minutes. The resolved peaks were collected, dried and sequenced.

The CNBr cleavage procedure resulted in six fragments which were resolved by RP-HPLC. An interferon peak eluting at about 40 minutes was sequenced and found to contain one sequence that aligned with that of CNBr fragment #3 which is composed of amino acids from position 22 to position 59 of IFN-α2b. The peak eluting at about 45 minutes contains a sequence that aligned with that of the CNBr fragment #5 which is composed of amino acids from position 112 to position 148 of IFN-α2 (common sequence for all IFN-α2 species). Another peak eluting at about 55 minutes contains a sequence that aligned with that of CNBr fragment #4 which is composed of amino acids from position 60 to position 111 of IFN-α2 (common sequence for all IFN-α2 species).

When the CNBr fragment #3 was further analyzed by tryptic digestion followed by RP-HPLC separation and sequencing, one major sequence and one minor sequence were detected. The major sequence was identified as IFN-α2b and the minor sequence corresponded to IFN-α2c, which indicates the presence of small amounts of IFN-α2c in peaks 1.1 and 1.2.

3. Results

The N-terminal sequences for unfractionated IFN-αn3a and the fractionated RP-HPLC peaks are presented in Table 10. The results shows that unfractionated alpha interferon, as well as individual interferon preparations, contain multiple sequences. All of these sequences are identified as human alpha interferon species.

TABLE 10

N-Terminal Sequence of IFNN α-n3a and RP-HPLC Peaks

| Cycle No. | α-n3a | 1.1 | 1.2 | 2 | 3 | 4 | 5 | 6 |
|---|---|---|---|---|---|---|---|---|
| 1 | ND* (C) | ND | ND | ND | ND | ND | ND | ND |
| 2 | D | D | D | D | D | D | D | D |
| 3 | L | L | L | L | L | L | L | L |
| 4 | P | P | P | P | P | P | P | P |
| 5 | Q | Q | Q | Q | Q | Q | Q | Q |
| 6 | T | T | T | T | T | T | T | T |
| 7 | H | H | H | H | H | H | H | H |
| 8 | S | S | S | S | S | S | S | S |
| 9 | L | L | L | L | L | L | L | L |
| 10 | G | G | G | G | G | G | G, R | G |
| 11 | N, S | S | S | N, S | N | N | N | N |
| 12 | R | R | R | R | R | R | R | R |
| 13 | R | R | R | R | R | R | R | R |
| 14 | A, T | T | T | A | A | A | A | A |
| 15 | L | L | L | L | L | L | L | L |
| 16 | I, M | M | M | I | I | I | I | I |
| 17 | L | L | L | L | L | L | L | L |
| 18 | L | L | L | L | L | L | L | L |
| 19 | A, G | A | A | A | G | A | A | A |
| 20 | Q | Q | Q | Q | Q | Q | Q | ND |
| 21 | M | M | M | M | M | M | M | M |
| 22 | R, G | R | R | G, R | G | R, G | G | R |
| 23 | R | R | R | R | R | R | R | R |
| 24 | I | I | I | I | ND | I | I | I |

TABLE 10-continued

N-Terminal Sequence of IFNN α-n3a and RP-HPLC Peaks

| Cycle No. | α-n3a | 1.1 | 1.2 | 2 | 3 | 4 | 5 | 6 |
|---|---|---|---|---|---|---|---|---|
| 25 | S | S | ND | S | ND | S | S | S |
| 26 | P | L | L | H | ND | P | P | P |
| 27 | F, P | P | P | F | ND | F | F | F |
| 28 | S | S | ND | S | ND | S | S | S |
| 29 | ND (C) | ND | ND | ND | ND | ND | ND | ND |
| 30 | ND | L | L | L | ND | L | L | L |
| 31 | ND | ND | K | ND | ND | K | ND | K |
| 32 | D | D | D | D | ND | D | D | D |
| 33 | R | R | R | R | ND | R | R | R |
| 34 | H | H | H | H | ND | H | H | H |
| SEQ ID No. | 1 | 2 | 3 | 4 | 5 | 6 | 7 | 8 |

*ND = Not Determined

The major species of interferon in each peak are shown in Table 11 below. The N-terminal sequences of the various separated peaks of IFN-αn3a are consistent with the interferon species recognized by NK2 monoclonal antibody as described by Celltech, Ltd.

TABLE 11

Major Interferon Species in Peaks

| Peak # | IFN Species |
|---|---|
| 1.1 | α2 (b/c) |
| 1.2 | α2 (b/c) |
| 2 | α4 (a/b); α16 |
| 3 | α10a |
| 4 | α8 (a/b/c); α21 (a/b); α17 (a/b/c/d) |
| 5 | α17 (a/b/c/d); α21 (a/b); α7 (a/b/c) |
| 6 | α8 (a/b/c) |

IFN-α2b is found primarily in interferon preparations 1.1 and 1.2, and in minor amounts in peak 2. IFN-α2c is found in small amounts in interferon preparation 1.1. IFN-α8(a/b/c) is found primarily in interferon peaks 4 and 6. Other interferon species presented in lesser amounts are α4(a/b) and/or α16, which are found in peak 2. Species α10a is found in interferon peak 3. Species α17(a/b/c) and/or α21 (a/b) are found primarily in peak 5, and in small amounts in peak 4. Species α7(a/b/c) are found primarily in peak 5 in low concentrations. Because the sequencing analyses were carried out to 30–35 cycles, it is difficult to distinguish some of the species which have sequence identity within these 30–35 cycles. The N-terminal sequences of all human interferon alpha species reported show that α21(a/b) and α17(a/b/c/d) have similar N-terminal sequences (up to amino acid position 33); so do α4(a/b) and α16 (up to amino acid position 33); and α2b as compared with α2c.

The minor differences that may exist in the amino acid sequence for the individual interferon proteins may be due to alpha interferon protein species differences, or genetic allelism. The latter may result in the appearance of a similar protein with an amino acid modification at a single site.

C. Carbohydrate Content

The carbohydrate content of the individual peaks was calculated as the ratio of moles sugar to moles alpha interferon protein [see, e.g., PCT Publication No. WO93/16107]. The unfractionated IFN-αn3a and individual interferon preparations contain carbohydrate which is in the range of 1–3 moles of sugar per mole of interferon. Interferon preparations containing IFN-α2, peaks 1.1 and 1.2, contain the most carbohydrate as compared with the later eluting interferon preparations. The IFN-α8(a/b/c)-containing preparation (peak 6) contains the least amount of carbohydrate. There is no detectable mannose or sialic acid in the later interferon peaks 3 to 6. This phenomenon is consistent with the hydrophobicity of the proteins. The lower content of the carbohydrate in the protein results in the higher hydrophobicity, and thus the protein is eluted later on RP-HPLC.

D. Carboxyl Terminus Amino Acid Sequencing

A protein sample (10–30 μg) was dialyzed against 50 mM sodium acetate at pH 5.5. Carboxypeptidase P was added at an enzyme:protein ratio of 1:100 (w/w). The mixture was incubated at 37° C. and aliquots were taken at 0.5, 1, 2, 5, 10 and 60 minutes. Each digestion and analysis was repeated at least twice.

The liberated amino acids from each time point were derivatized with O-phataldehyde (OPA) in 2% SDS/0.4M lithium borate for 30 seconds. The derivatized amino acids were separated on a C18 reverse phase Pico-Tag column using a methanol gradient against a sodium acetate/tetrahydrofurane/water buffer. Identification and quantification of released amino acids was done by comparison to an HPLC profile of OPA derivatized standard amino acids.

The results from C-terminal sequencing analyses for IFN-αn3a, RP-HPLC interferon preparations and alpha-interferon species are summarized in Table 12.

TABLE 12

C-Terminal Sequences of alpha-Interferon Species, IFN α-n3a and RP-HPLC Peaks

| Subtypes | SEQ ID | Cycles | | | | |
|---|---|---|---|---|---|---|
| IFN-α | NO. | −5 | −4 | −3 | −2 | −1 |
| Concensus | 9 | L | R | R | K | D |
| α2 (b/c) | 10 | L | R | S | K | E |
| α8 (a/b/c) | 11 | L | K | S | K | E |
| α4 (a/b) | 12 | L | R | R | K | D |
| α10a | 13 | L | R | R | K | D |
| α21 (a/b) | 14 | L | R | R | K | E |
| α7 (a/b/c/d) | 15 | L | R | R | K | D |
| IFN α-n3a | 16 | L | R | S (R) | K | E |
| Peak 1.1 | 17 | L | R | S | K | E |
| Peak 1.2 | 18 | L | R | S | K | E |
| Peak 3 | 19 | L | R | R/K | K/R | D |
| Peak 5 | 20 | L | R | R | K/R | D |
| Peak 6 | 21 | ND | ND | S | K | E |

ND = Not Determined

The sequence was identified bed on the order of appearance and plateau of the individual amino acid residues. For example glutamic acid appears and plateaus earlier than other residues, and hence it is determined as the first residue from the C-terminus. Sequences from other cycles were determined using a similar principle. In the case of unfractionated alpha interferon, the major C-terminal sequence was determined as Leu-Arg-(Ser/Arg)-Lys-Glu [SEQ ID NO: 16].

The theoretical sequences for those alpha interferon species are also presented in Table 12 for comparison. The results show that the major C-terminal sequence for interferon preparations 1.1 and 1.2 as well as the unfractionated interferon is similar to that of IFN-α2b. This demonstrates that unfractionated interferon and interferon preparations 1.1 and 1.2 contain intact carboxyl termini. The C-terminal sequencing analysis used here is much less sensitive than the N-terminal sequencing. Any minor difference may not be detected. For instance, α8 C-terminal residues (Leu-Lys-Ser-Lys-Glu) [SEQ ID NO: 22] were not detected in the presence of major IFN-α2b C-terminal residues (Leu-Arg-Ser-Lys-Glu) [SEQ ID NO: 23], where the two sequences only differ at cycle −4. The presence of a minor interferon component with a truncated C-terminus was not detected if the amount of component is less than 20%.

EXAMPLE 7

ANTI-HIV-1 ACTIVITY

Interferon α2 species proteins are known to have antiviral effects, both in vivo and in vitro. The interferon species and mixtures isolated from IFN-αn3a were examined for their antiviral activity against Human Immunodeficiency Virus 1 (HIV-1) in a series of in vitro assays.

A. Cell Culture and Reverse Transcriptase Assays

The cells used in these studies were normal human monocytes recovered from peripheral blood mononuclear cells (PBMC) of HIV and hepatitis B sero-negative donors after leukaphoresis and purified by counter current centrifugal elutriation of mononuclear leukocyte-rich fractions of blood cells. The cell suspensions were assayed and found to be >98% monocytes and were cultured as adherent monolayers ($1.5 \times 10^5$ cells/ml) in DMEM (Gibco, Grand Island, N.Y.) with 10% heat-inactivated A+ human serum, 50 μg/ml gentamycin, and 1000 U/ml highly purified recombinant M-CSF (FAP-809, Cetus Corp., Emeryville, Calif.). All culture reagents were tested and found to be negative for endotoxin contamination.

The adherent monocytes were cultured for 7 days in the absence of interferon, and prior to the addition of a monocyte tropic HIV-1 strain (ADA). The infected cells were incubated for up to four (4) weeks of culture in the presence or absence of added interferon. Culture medium was half-exchanged every 2 to 3 days.

The interferon used in these experiments, were of different sources and hence were first titered against another virus, i.e., Vesicular Stomatitis Virus (VSV) in a CPE assay using MDBK cells. The interferons were normalized in this CPE assay, to the same number of antiviral units/ml of culture for these experiments. When IFN is added at the same time as the virus, or just before, there is a dose dependent inhibition of HIV production by the interferon.

Reverse transcriptase (RT) activity in replicate cell cultures, and associated with the HIV-1 virus was used to quantitate the levels of viral expression in these experiments. Tissue culture fluids, collected at different times, were added to a reaction mixture consisting of 0.05% Nonidet P-40 (Sigma Chemical Co.), 10 μg/ml poly (A) , 0.25 U/ml oligo dT (Pharmacia, Piscataway, N.J.), 5 mM dithiothreitol (Pharmacia), 150 mM KCl, 15 mM $MgCl_2$ and $^3H$-dTTP (2 Ci/mmol, Amersham Corp., Arlington Heights Ill.) in pH 7.9 TRIS-HCl buffer for 24 hours at 37° C. Incorporated radioactivity was precipitated with cold TCA, washed and collected in an automatic cell harvester (Skatron, Inc., Sterling, Va.) on glass filter disks. Radioactivity was measured in a liquid scintillation counter.

B. Anti HIV-1 Activity of Separated Peaks

The anti HIV-1 activity of the reverse phase HPLC fractionated interferon preparations were examined in the monocyte culture assays. IFN-αn3a was fractionated on a RP-HPLC column as described previously and each RP-HPLC interferon preparation of IFN activity was normalized for its antiviral (i.e., VSV) CPE activity in MDBK cells prior to use in these experiments. Six interferon preparations were examined in these studies, that is, the interferon preparations identified in Table 11 above as peaks 1 (1.1 and 1.2 taken together), 2, 3, 4, 5, and 6 after normalization of CPE titer. One hundred (100) IU/ml and HIV-1 moi of ≦0.02 were used for each of the assays. The results are presented in Table 13 and in FIG. 2.

TABLE 13

Relative Ratio of Anti-HIV-1 Activity of RP-HPLC Peaks

| IFN Added (100 IU/ml) | | | | Peaks | | | |
|---|---|---|---|---|---|---|---|
| | None | 1 | 2 | 3 | 4 | 5 | 6 |
| HIV-1 Activity Inhibited | 0% | 26% | 95% | 75% | 87% | 88% | 98% |

These results show that substantial anti-HIV-1 activity resides in the IFN compositions of RP-HPLC interferon preparations containing little or no IFN-α2. Specifically, the interferon preparation containing only α8 demonstrated the highest anti viral activity. In fact, from a review of FIG. 2, it can be seen that the interferon compositions containing little or no IFN-α2, were at least 3–40 fold more effective in reducing viral activity. For example, while treatment with peak 1 left 74% of total viral activity; peak 6 left only 2% of total viral activity, when the compositions were used in equivalent amounts. This is in complete contrast to previous teachings of the art (see Sherber et al, cited above).

Additionally, the interferon preparation containing substantially all IFN-α4 and/or IFN-α16, with only small amounts of IFN-α2, that is, less than 30% by weight, demonstrated similar high activity. The other interferon preparations identified above as containing no detectable amount of IFN-α2 also demonstrated strong but lesser activities.

Interestingly, and unexpected was the finding that the IFN-α2(b/c) in RP-HPLC interferon preparation 1 had the least anti retroviral activity of the species examined.

While certain embodiments of the invention have been particularly described, it will be apparent to those skilled in the art that many modifications and variations may be made. For example, it may be possible to prepare antiviral compositions containing at least 45% by weight of an IFN-α2 protein as the selected antiviral agent to which the present compositions are added as additives. It is contemplated that greater amounts of the selected antiviral agent may be employed, where the compositions of this invention are used as additives. Therefore, the present invention is not to be construed as limited by any of the particular embodiments shown, rather its scope will be defined only by the claims which follow.

What is claimed is:

1. A pharmaceutical composition comprising a natural human leukocyte alpha interferon (IFN) species protein selected from the group consisting of IFN-α4a, IFN-α4b, IFN-α7a, IFN-α7c, IFN-α8a, IFN-α8b, IFN-α8c, IFN-α10a, IFN-α16, IFN-α17a, IFN-α17b, IFN-α17c, IFN-α17d, IFN-α21a, IFN-α21b and combinations thereof, in a pharmaceutically acceptable carrier, said composition containing substantially no IFN-α2a, IFN-α2b or IFN-α2c and characterized by an anti-viral activity greater than that of IFN-α2a, IFN-α2b, or IFN-α2c.

2. The composition according to claim 1 consisting essentially of the alpha IFN species of peak 6 of Table 11, corresponding to at least one specie selected from the group consisting of IFN-α8a, IFN-α8b, IFN-α8c and combinations thereof.

3. The composition according to claim 1 consisting essentially of IFN-α8b.

4. The composition according to claim 1 consisting essentially of the alpha IFN species of peak 2 of Table 11, corresponding to at least one protein selected from the group consisting of IFN-α4a, IFN-α4b, IFN-α16, and combinations thereof.

5. The composition according to claim 1 consisting essentially of the alpha IFN species of peak 5 of Table 11, corresponding to at least one protein selected from the group consisting of IFN-α7a, IFN-α7b, IFN-α7c, IFN-α17a, IFN-α17b, IFN-α17c, IFN-α17d, IFN-α21a, IFN-α21b, and combinations thereof.

6. The composition according to claim 1 consisting essentially of an effective amount of the alpha IFN species of peak 4 of Table 11, corresponding to a protein selected from the group consisting of IFN-α8a, IFN-α8b, IFN-α8c, IFN-α17a, IFNα17b, IFN-α17c, IFN-α17d, IFN-α21a, IFN-α21b, and combinations thereof.

7. The composition according to claim 1 consisting essentially of IFN-α10a.

8. A pharmaceutical composition comprising a mixture of natural human leukocyte alpha interferon (IFN) species proteins in a pharmaceutically acceptable carrier, said mixture comprising at least two selected from the group consisting of:

(a) the IFN species corresponding to peak 2 of Table 11, selected from the group consisting of IFNα4a, IFN-α4b, and IFN-α16;

(b) the IFN species corresponding to peak of Table 11, IFN-α10a;

(c) the IFN species corresponding to peak 4 of Table 11, selected from the group consisting of IFN-α8a, IFN-α8b, IFN-α8c, IFN-α21a, IFN-α21b, IFN-α17a, IFN-α17b, IFN-α17c, and IFN-α17d;

(d) the IFN species corresponding to peak 5 of Table 11, selected from the group consisting of IFN-α7a, IFN-α7b, IFN-α7c, IFN-α17a, IFN-α17b, IFN-α17c, IFN-α17d, IFN-α21a, and IFN-α21b;

(e) the IFN species corresponding to peak 6 of Table 11, selected from the group consisting of IFN-α8a, IFN-α8b, and IFN-α8c;

wherein said composition contains substantially no IFN-α1, IFN-α2a, IFN-α2b, IFN-α2c, IFN-α5, IFN-α6, IFN-α10b, IFN-α13, IFN-α14, or IFN-α22 and is characterized by an anti viral activity greater than that of IFN-α2a, IFN-α2b, or IFN-α2c.

9. A method of treating a retroviral infection i a mammalian host comprising administering to said host a pharmaceutically effective amount of a composition of claim 1.

10. The method according to claim 9 wherein the retrovirus is selected from the group consisting of HIV 1, HIV 2, HTLV I and HTLV II.

11. A method of treating a viral hepatitis infection in a mammalian host comprising administering to said host a pharmaceutically effective amount of the composition of claim 1.

12. The method according to claim 11 wherein said hepatitis infection is selected from the group consisting of Hepatitis A, Hepatitis B, Hepatitis C, Hepatitis D, and Hepatitis E.

13. A method for enhancing the potency of an antiviral agent comprising adding to said antiviral agent an effective amount of the composition of claim 1.

14. A pharmaceutical composition comprising an effective amount of an antiviral additive composition comprising the composition of claim 1, in admixture with a selected second antiviral agent, said pharmaceutical composition characterized by an anti viral specific activity greater than that of the second antiviral agent alone.

15. The composition according to claim 14 wherein said effective amount is at least 1% by weight.

16. The composition according to claim 14 wherein said effective amount is at least 5% by weight.

17. The composition according to claim 14 wherein said antiviral additive composition consists essentially of the alpha IFN mixture of peak 6 of Table 11, corresponding to at least one specie selected from the group consisting of IFN-α8a, IFN-α8b, IFN-α8c and combinations thereof.

18. The composition according to claim 14 wherein said antiviral additive composition consists essentially of IFN-α8b.

19. The composition according to claim 14 wherein said antiviral additive composition consists essentially of the alpha IFN species of peak 2 of Table 11, corresponding to at least one protein selected from the group consisting of IFN-α4a, IFN-α4b, IFN-α16, and combinations thereof.

20. The composition according to claim 14 wherein said antiviral additive composition consists essentially of the alpha IFN species of peak 5 of Table 11, corresponding to at least one protein selected from the group consisting of IFN-α7a, IFN-α7b, IFN-α7c, IFN-α17a, IFN-α17b, IFN-α17c, IFN-α17d, IFNα21a, IFN-α21b, and combinations thereof.

21. The composition according to claim 14 wherein said antiviral additive composition consists essentially of the alpha IFN species of peak 4 of Table 11, corresponding to a protein selected from the group consisting of IFN-α8a, IFN-α8b, IFN-α8c, IFN-α17a, IFN-α17b, IFN-α17c, IFN-α17d, IFN-α21a, IFN-α21b, and combinations thereof.

22. The composition according to claim 14 wherein said antiviral agent consists essentially of IFN-α10a.

* * * * *

UNITED STATES PATENT AND TRADEMARK OFFICE
CERTIFICATE OF CORRECTION

PATENT NO. : 5,676,942
DATED : October 14, 1997
INVENTOR(S) : Douglas Testa, Mei-June Liao, Katalin Ferencz-Biro, Abbas Rashidbaigi, and Mario DiPaola It is certified that error appears in the above-identified patent and that said Letters Patent is hereby corrected as shown below:

Col. 1, in Table 1, first column under heading "Letter", line 50, before "G", insert -- α --.

Col. 1, in Table 1, fourth column under heading "Numerical", line 50, before "88", insert -- α --.

Col. 1, in Table 1, third column under heading "Letter", line 52, before "II", insert -- α --.

Col. 2, line 31, first instance, delete "INF" and insert in place thereof -- IFN --.

Col. 3, line 26, delete "Eke" and insert in place thereof -- the --.

Col. 6, line 1, delete "interforth" and insert in place thereof -- interferon --.

Col. 13, line 32, delete "*Chromatoaraphic*" and insert in place thereof -- *Chromatographic* --.

Col. 14, line 50, delete "Antioroliferative" and insert in place thereof -- Antiproliferative --.

Col. 16, line 16, delete "(1979)" and insert in place thereof -- (1970) --.

Col. 16, line 27, delete "Table" and insert in place thereof -- Tables --.

UNITED STATES PATENT AND TRADEMARK OFFICE
CERTIFICATE OF CORRECTION

PATENT NO. : 5,676,942
DATED : October 14, 1997
INVENTOR(S) : Douglas Testa, Mei-June Liao, Katalin Ferencz-Biro, Abbas Rashidbaigi, and Mario DiPaola It is certified that error appears in the above-identified patent and that said Letters Patent is hereby corrected as shown below:

Col. 19, in Table 9, in column 12 under the subheading "17a", third line, delete "154" and insert in place thereof -- 14 --.

Col. 19, in Table 9, in column 12 under the subheading "17a", fourteenth line, insert -- 9 --.

Col. 20, in the second section of Table 9, in column 8 under the subheading "5", eighth line, delete "8.7" and insert in place thereof -- 9.7 --.

Col. 20, in the second section of Table 9, in column 9 under the subheading "6", eighth line, delete ".0" and insert in place thereof -- 9.0 --.

Col. 23, line 53, delete "bed" and insert in place thereof -- based --.

Col. 38, in Claim 8, paragraph (b), line 1, after "peak", insert -- 3 --.
Col. 39, in claim 9, line 1, delete "i" and insert in place thereof --in--

Signed and Sealed this

Twenty-fourth Day of March, 1998

Attest:

BRUCE LEHMAN

*Attesting Officer*  Commissioner of Patents and Trademarks

UNITED STATES PATENT AND TRADEMARK OFFICE
CERTIFICATE OF CORRECTION

PATENT NO.   : 5,676,942
DATED        : October 14, 1997
INVENTOR(S)  : Douglas Testa, Mei-June Liao, Katalin Ferencz-Biro, Abbas Rashidbaigi, and Mario DiPaola It is certified that error appears in the above-indentified patent and that said Letters Patent is hereby corrected as shown below:

Col. 37, Claim 1, line 4, after "IFN-α7a,", insert -- IFN-α7b, --.

Signed and Sealed this

Twenty-eighth Day of April, 1998

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( D ) TOPOLOGY: unknown ( i i ) MOLECULE TYPE: protein ( i x ) FEATURE:
        ( A ) NAME/KEY: Region
        ( B ) LOCATION: 1
        ( D ) OTHER INFORMATION: /note= "this amino acid may be Cys"

( i x ) FEATURE:
        ( A ) NAME/KEY: Region
        ( B ) LOCATION: 11
        ( D ) OTHER INFORMATION: /note= "this amino acid may also be Ser"

( i x ) FEATURE:
        ( A ) NAME/KEY: Region
        ( B ) LOCATION: 14
        ( D ) OTHER INFORMATION: /note= "this amino acid may also be Thr"

( i x ) FEATURE:
        ( A ) NAME/KEY: Region
        ( B ) LOCATION: 16
        ( D ) OTHER INFORMATION: /note= "this amino acid may also be Met"

( i x ) FEATURE:
        ( A ) NAME/KEY: Region (B) LOCATION: 19
(D) OTHER INFORMATION: /note= "this amino acid may also be Gly"

(ix) FEATURE:
(A) NAME/KEY: Region
(B) LOCATION: 22
(D) OTHER INFORMATION: /note= "this amino acid may also be Gly"

(ix) FEATURE:
(A) NAME/KEY: Region
(B) LOCATION: 27
(D) OTHER INFORMATION: /note= "this amino acid may also be Pro"

(ix) FEATURE:
(A) NAME/KEY: Region
(B) LOCATION: 29
(D) OTHER INFORMATION: /note= "this amino acid may be Cys"

(xi) SEQUENCE DESCRIPTION: SEQ ID NO:1:

```
Xaa Asp Leu Pro Gln Thr His Ser Leu Gly Asn Arg Arg Ala Leu Ile
1               5                   10                  15
Leu Leu Ala Gln Met Arg Arg Ile Ser Pro Phe Ser Xaa Xaa Xaa Asp
            20                  25                  30
Arg His
```

(2) INFORMATION FOR SEQ ID NO:2:

(i) SEQUENCE CHARACTERISTICS:
(A) LENGTH: 34 amino acids
(B) TYPE: amino acid
(D) TOPOLOGY: unknown (ii) MOLECULE TYPE: protein (xi) SEQUENCE DESCRIPTION: SEQ ID NO:2:

```
Xaa Asp Leu Pro Gln Thr His Ser Leu Gly Ser Arg Arg Thr Leu Met
1               5                   10                  15
Leu Leu Ala Gln Met Arg Arg Ile Ser Leu Pro Xaa Xaa Leu Xaa Asp
            20                  25                  30
Arg His
```

(2) INFORMATION FOR SEQ ID NO:3:

(i) SEQUENCE CHARACTERISTICS:
(A) LENGTH: 34 amino acids
(B) TYPE: amino acid
(D) TOPOLOGY: unknown (ii) MOLECULE TYPE: protein (xi) SEQUENCE DESCRIPTION: SEQ ID NO:3:

```
Xaa Asp Leu Pro Gln Thr His Ser Leu Gly Ser Arg Arg Thr Leu Met
1               5                   10                  15
Leu Leu Ala Gln Met Arg Arg Ile Xaa Leu Pro Ser Xaa Leu Lys Asp
            20                  25                  30
Arg His
```

(2) INFORMATION FOR SEQ ID NO:4:

(i) SEQUENCE CHARACTERISTICS:
(A) LENGTH: 34 amino acids
(B) TYPE: amino acid
(D) TOPOLOGY: unknown (ii) MOLECULE TYPE: protein (ix) FEATURE:
    (A) NAME/KEY: Region
    (B) LOCATION: 11
    (D) OTHER INFORMATION: /note= "this amino acid may also be Ser"

(ix) FEATURE:
    (A) NAME/KEY: Region
    (B) LOCATION: 22
    (D) OTHER INFORMATION: /note= "this amino acid may also be Arg"

(xi) SEQUENCE DESCRIPTION: SEQ ID NO:4:

Xaa Asp Leu Pro Gln Thr His Ser Leu Gly Asn Arg Arg Ala Leu Ile
1               5                   10                  15

Leu Leu Ala Gln Met Gly Arg Ile Ser His Phe Ser Xaa Leu Xaa Asp
            20                  25                  30

Arg His (2) INFORMATION FOR SEQ ID NO:5:

(i) SEQUENCE CHARACTERISTICS:
        (A) LENGTH: 34 amino acids
        (B) TYPE: amino acid
        (D) TOPOLOGY: unknown (ii) MOLECULE TYPE: protein (xi) SEQUENCE DESCRIPTION: SEQ ID NO:5:

Xaa Asp Leu Pro Gln Thr His Ser Leu Gly Asn Arg Arg Ala Leu Ile
1               5                   10                  15

Leu Leu Gly Gln Met Gly Arg Xaa Xaa Xaa Xaa Xaa Xaa Xaa Xaa Xaa
            20                  25                  30

Xaa Xaa (2) INFORMATION FOR SEQ ID NO:6:

(i) SEQUENCE CHARACTERISTICS:
        (A) LENGTH: 34 amino acids
        (B) TYPE: amino acid
        (D) TOPOLOGY: unknown (ii) MOLECULE TYPE: protein (ix) FEATURE:
        (A) NAME/KEY: Region
        (B) LOCATION: 22
        (D) OTHER INFORMATION: /note= "this amino acid may also be Gly"

(xi) SEQUENCE DESCRIPTION: SEQ ID NO:6:

Xaa Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Xaa Leu Lys Asp
            20                  25                  30

Arg His (2) INFORMATION FOR SEQ ID NO:7:

(i) SEQUENCE CHARACTERISTICS:
        (A) LENGTH: 34 amino acids
        (B) TYPE: amino acid
        (D) TOPOLOGY: unknown (ii) MOLECULE TYPE: protein (ix) FEATURE:

( A ) NAME/KEY: Region
( B ) LOCATION: 10
( D ) OTHER INFORMATION: /note= "this amino acid may also be Arg"

( x i ) SEQUENCE DESCRIPTION: SEQ ID NO:7:

```
Xaa Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Xaa Leu Xaa Asp
            20                  25                  30

Arg His
```

( 2 ) INFORMATION FOR SEQ ID NO:8:

( i ) SEQUENCE CHARACTERISTICS:
    ( A ) LENGTH: 34 amino acids
    ( B ) TYPE: amino acid
    ( D ) TOPOLOGY: unknown ( i i ) MOLECULE TYPE: protein ( x i ) SEQUENCE DESCRIPTION: SEQ ID NO:8:

```
Xaa Asp Leu Pro Gln Thr His Ser Leu Gly Asn Arg Arg Ala Leu Ile
1               5                   10                  15

Leu Leu Ala Xaa Met Arg Arg Ile Ser Pro Phe Ser Xaa Leu Lys Asp
            20                  25                  30

Arg His
```

( 2 ) INFORMATION FOR SEQ ID NO:9:

( i ) SEQUENCE CHARACTERISTICS:
    ( A ) LENGTH: 5 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:9:

```
Leu Arg Arg Lys Asp
1               5
```

( 2 ) INFORMATION FOR SEQ ID NO:10:

( i ) SEQUENCE CHARACTERISTICS:
    ( A ) LENGTH: 5 amino acids
    ( B ) TYPE: amino acid
    ( D ) TOPOLOGY: unknown ( i i ) MOLECULE TYPE: protein ( x i ) SEQUENCE DESCRIPTION: SEQ ID NO:10:

```
Leu Arg Ser Lys Glu
1               5
```

( 2 ) INFORMATION FOR SEQ ID NO:11:

( i ) SEQUENCE CHARACTERISTICS:
    ( A ) LENGTH: 5 amino acids
    ( B ) TYPE: amino acid
    ( D ) TOPOLOGY: unknown ( i i ) MOLECULE TYPE: protein ( x i ) SEQUENCE DESCRIPTION: SEQ ID NO:11:

```
Leu Lys Ser Lys Glu
1               5
```

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:12:

```
Leu  Arg  Arg  Lys  Asp
1                   5
```

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:13:

```
Leu  Arg  Arg  Lys  Asp
1                   5
```

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:14:

```
Leu  Arg  Arg  Lys  Glu
1                   5
```

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:15:

```
Leu  Arg  Arg  Lys  Asp
1                   5
```

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( D ) TOPOLOGY: unknown ( i i ) MOLECULE TYPE: protein ( i x ) FEATURE:
        ( A ) NAME/KEY: Region
        ( B ) LOCATION: 3
        ( D ) OTHER INFORMATION: /note= "this amino acid may also be
            Arg"

( x i ) SEQUENCE DESCRIPTION: SEQ ID NO:16:

```
Leu  Arg  Ser  Lys  Glu
```

-continued

```
        1               5
```

(2) INFORMATION FOR SEQ ID NO:17:

(i) SEQUENCE CHARACTERISTICS:
        (A) LENGTH: 5 amino acids
        (B) TYPE: amino acid
        (D) TOPOLOGY: unknown (ii) MOLECULE TYPE: protein (xi) SEQUENCE DESCRIPTION: SEQ ID NO:17:

```
Leu  Arg  Ser  Lys  Glu
1                     5
```

(2) INFORMATION FOR SEQ ID NO:18:

(i) SEQUENCE CHARACTERISTICS:
        (A) LENGTH: 5 amino acids
        (B) TYPE: amino acid
        (D) TOPOLOGY: unknown (ii) MOLECULE TYPE: protein (xi) SEQUENCE DESCRIPTION: SEQ ID NO:18:

```
Leu  Arg  Ser  Lys  Glu
1                     5
```

(2) INFORMATION FOR SEQ ID NO:19:

(i) SEQUENCE CHARACTERISTICS:
        (A) LENGTH: 5 amino acids
        (B) TYPE: amino acid
        (D) TOPOLOGY: unknown (ii) MOLECULE TYPE: protein (ix) FEATURE:
        (A) NAME/KEY: Region
        (B) LOCATION: 3
        (D) OTHER INFORMATION: /note= "this amino acid may also be
            Lys"

(ix) FEATURE:
        (A) NAME/KEY: Region
        (B) LOCATION: 4
        (D) OTHER INFORMATION: /note= "this amino acid may also be
            Arg"

(xi) SEQUENCE DESCRIPTION: SEQ ID NO:19:

```
Leu  Arg  Arg  Lys  Asp
1                     5
```

(2) INFORMATION FOR SEQ ID NO:20:

(i) SEQUENCE CHARACTERISTICS:
        (A) LENGTH: 5 amino acids
        (B) TYPE: amino acid
        (D) TOPOLOGY: unknown (ii) MOLECULE TYPE: protein (ix) FEATURE:
        (A) NAME/KEY: Region
        (B) LOCATION: 4
        (D) OTHER INFORMATION: /note= "this amino acid may also be
            Arg"

(xi) SEQUENCE DESCRIPTION: SEQ ID NO:20:

```
Leu  Arg  Arg  Lys  Asp
1                     5
```

(2) INFORMATION FOR SEQ ID NO:21:

(i) SEQUENCE CHARACTERISTICS:
      (A) LENGTH: 5 amino acids
      (B) TYPE: amino acid
      (D) TOPOLOGY: unknown (ii) MOLECULE TYPE: protein (xi) SEQUENCE DESCRIPTION: SEQ ID NO:21:

Xaa  Xaa  Ser  Lys  Glu
   1                      5

(2) INFORMATION FOR SEQ ID NO:22:

(i) SEQUENCE CHARACTERISTICS:
      (A) LENGTH: 5 amino acids
      (B) TYPE: amino acid
      (D) TOPOLOGY: unknown (ii) MOLECULE TYPE: protein (xi) SEQUENCE DESCRIPTION: SEQ ID NO:22:

Leu  Lys  Ser  Lys  Glu
   1                      5

(2) INFORMATION FOR SEQ ID NO:23:

(i) SEQUENCE CHARACTERISTICS:
      (A) LENGTH: 5 amino acids
      (B) TYPE: amino acid
      (D) TOPOLOGY: unknown (ii) MOLECULE TYPE: protein (xi) SEQUENCE DESCRIPTION: SEQ ID NO:23:

Leu  Arg  Ser  Lys  Glu
   1                      5